US012611385B2

(12) United States Patent
Li et al.

(10) Patent No.: US 12,611,385 B2
(45) Date of Patent: Apr. 28, 2026

(54) USE OF TWO-DIMENSIONAL NANOMATERIAL IN INHIBITION OF CORONAVIRUS

(71) Applicants: SHENZHEN INSTITUTES OF ADVANCED TECHNOLOGY, Guangdong (CN); INSTITUTE OF HIGH ENERGY PHYSICS, CAS, Beijing (CN)

(72) Inventors: Yang Li, Guangdong (CN); Liming Wang, Guangdong (CN); Guofang Zhang, Guangdong (CN)

(73) Assignees: SHENZHEN INSTITUTES OF ADVANCED TECHNOLOGY;, Guangdong (CN); INSTITUTE OF HIGH ENERGY PHYSICS, CAS, Beijing (CN)

( * ) Notice: Subject to any disclaimer, the term of this patent is extended or adjusted under 35 U.S.C. 154(b) by 281 days.

(21) Appl. No.: 18/267,783

(22) PCT Filed: Feb. 22, 2021

(86) PCT No.: PCT/CN2021/077226
§ 371 (c)(1),
(2) Date: Jun. 16, 2023

(87) PCT Pub. No.: WO2022/126857
PCT Pub. Date: Jun. 23, 2022

(65) Prior Publication Data
US 2024/0091167 A1     Mar. 21, 2024

(30) Foreign Application Priority Data

Dec. 17, 2020     (CN) .......................... 202011495254.7
Feb. 10, 2021     (CN) .......................... 202110183434.X

(51) Int. Cl.
A61K 33/24     (2019.01)
A01N 25/34     (2006.01)
(Continued)

(52) U.S. Cl.
CPC ............ *A61K 9/7007* (2013.01); *A01N 25/34* (2013.01); *A01N 59/00* (2013.01); *A01N 59/16* (2013.01);
(Continued)

(58) Field of Classification Search
CPC ...... A61K 9/7007; A61K 33/24; A61K 33/42; A61K 33/44; A61K 45/06; A61K 8/19;
(Continued)

(56) References Cited

U.S. PATENT DOCUMENTS

2017/0049814 A1     2/2017  Sawosz Chwalibog et al.
2020/0330928 A1*   10/2020  Thalappil ............. B01D 71/022

FOREIGN PATENT DOCUMENTS

CA     3097636     4/2021
CN     102173145   9/2011
(Continued)

OTHER PUBLICATIONS

Feng et al. (Public Health 2020;183:4-5). (Year: 2020).*
(Continued)

*Primary Examiner* — Ernst V Arnold
(74) *Attorney, Agent, or Firm* — Sang Young Han

(57)     ABSTRACT

Provided is the use of two-dimensional nanomaterials in the inhibition of a coronavirus, and specifically disclosed is the use of the two-dimensional nanomaterials in the preparation of a medicament for treating or preventing diseases caused by a coronavirus or of a material for adhering to or inhibiting the coronavirus. The two-dimensional nanomaterial is selected from the group consisting of copper indium thiophosphate (CIPS) nanosheet, graphene oxide nanosheet,
(Continued)

molybdenum disulfide nanosheet, black phosphorus nanosheet and mixtures thereof. The coronavirus is selected from one of HCoV-229E, HCoV-OC43, HCoV-NL63, HCoV-HKU1, SARS-CoV, SARS-CoV2 or MERS-CoV. The diseases caused by the coronavirus are diseases caused by coronavirus infection. The material has the advantages of being simple to prepare, having a high biological safety and an excellent effect.

9 Claims, 13 Drawing Sheets

(51) Int. Cl.

| | |
|---|---|
| *A01N 59/00* | (2006.01) |
| *A01N 59/16* | (2006.01) |
| *A01N 59/26* | (2006.01) |
| *A01P 1/00* | (2006.01) |
| *A61K 9/70* | (2006.01) |
| *A61K 33/42* | (2006.01) |
| *A61K 33/44* | (2006.01) |
| *A61K 45/06* | (2006.01) |
| *A61P 31/14* | (2006.01) |
| *B82Y 5/00* | (2011.01) |

(52) U.S. Cl.
CPC ................ *A01N 59/26* (2013.01); *A01P 1/00* (2021.08); *A61K 33/24* (2013.01); *A61K 33/42* (2013.01); *A61K 33/44* (2013.01); *A61K 45/06* (2013.01); *A61P 31/14* (2018.01); *B82Y 5/00* (2013.01)

(58) Field of Classification Search
CPC .......... A61K 8/24; A61K 33/30; A01N 25/34; A01N 59/00; A01N 59/16; A01N 59/26; A01P 1/00; A61P 31/14; B82Y 5/00; Y02A 50/30; C09D 5/14; C11D 3/48; C11D 3/12; A41D 31/30; A61Q 19/10; B01D 39/20; B01D 46/00; B65D 65/38
See application file for complete search history.

(56) References Cited

FOREIGN PATENT DOCUMENTS

| | | | | |
|---|---|---|---|---|
| CN | 108144059 | 6/2018 | | |
| CN | 108707382 | 10/2018 | | |
| CN | 110179769 A | * 8/2019 | .......... | A61K 9/5176 |
| CN | 110364572 | 10/2019 | | |
| CN | 111110899 | 5/2020 | | |
| CN | 111617103 | 9/2020 | | |
| CN | 111789131 | 10/2020 | | |
| CN | 111820502 | 10/2020 | | |
| CN | 111903707 | 11/2020 | | |
| CN | 112220919 | 1/2021 | | |
| WO | WO-2017186809 A1 | * 11/2017 | .......... | A61K 47/645 |
| WO | 2018029365 | 2/2018 | | |
| WO | 2019077635 | 4/2019 | | |

OTHER PUBLICATIONS

Mawazi et al. (American Journal of Emergency Medicine 85 (2024) 98-107). (Year: 2024).*
English translation of CN111820502A 2020; 11 pages. (Year: 2020).*
Zhang et al. ([online] retrieved on Jul. 7, 2025 from: https://www.biorxiv.org/content/biorxiv/early/2021/04/14/2021.04.13.439641.full.pdf; Apr. 14, 2021: 36 pages.) (Year: 2021).*
English translation CN110179769; 2019: 5 pages. (Year: 2019).*
English translation CN108339022; 2018: 9 pages. (Year: 2018).*
English translation CN111903707; 2020; 9 pages. (Year: 2020).*
Jin, Xiulong et al., "Progress in Antibacterial and Antiviral Research of Graphene Materials", Advanced Materials Industry, Apr. 2020, with Partial English translation, 9 pages.
Fucai Liu et al., "Room-temperature ferroelectricity in CuInP2S6 ultrathin flakes", Nature Communication, Aug. 2016, pp. 1-6.
"International Search Report (Form PCT/ISA/210) of PCT/CN2021/077226," mailed on Sep. 16, 2021, with English translation thereof, pp. 1-8.

* cited by examiner

USE OF TWO-DIMENSIONAL NANOMATERIAL IN INHIBITION OF CORONAVIRUS

CROSS-REFERENCE TO RELATED APPLICATION

This application is a 371 of international application of PCT application serial no. PCT/CN2021/077226, filed on Feb. 22, 2021, which claims the priority benefit of China application no. 202011495254.7 and 202110183434.X, filed on Dec. 17, 2020 and Feb. 10, 2021, respectively. The entirety of each of the above-mentioned patent applications is hereby incorporated by reference herein and made a part of this specification.

BACKGROUND OF THE INVENTION

1. Technical Field

The present invention relates to the technical field of antivirus, in particular to use of a two-dimensional nanomaterial in the inhibition of a coronavirus.

2. Background Art

Nanomaterial refers to a material that reaches a nanoscale in a certain one-dimensional, two-dimensional, or three-dimensional direction. The nanomaterial can be divided into zero-dimensional material, one-dimensional material, two-dimensional material and three-dimensional material. The two-dimensional material refers to a material in which electrons can conduct free motion (planar motion) only in a nanoscale of two dimensions, such as boron nitride (BN) nanosheet, molybdenum disulfide ($MoS_2$) nanosheet, tungsten disulfide ($WS_2$) nanosheet, and a Mxene material. The two-dimensional nanomaterial has carriers whose migration and thermal diffusion are limited in the two-dimensional plane, thereby showing many unique properties and being widely applied in the electronic field. But the application in the medical field is still uncommon.

Coronavirus is a large virus family known to cause the common cold and more severe diseases such as Middle East Respiratory Syndrome (MERS) and Severe Acute Respiratory Syndrome (SARS). 2019 novel coronavirus (2019-nCoV, causing novel coronavirus pneumonia COVID-19) is the 7th currently known coronavirus, after HCoV-229E, HCoV-OC43, HCoV-NL63, HCoV-HKU1, SARS-CoV (causing severe acute respiratory syndrome) and MERS-CoV (causing Middle East respiratory syndrome), and no effective medicaments are currently available.

At the present stage, nanodrug and related formulations that can significantly inhibit the cell infection of coronavirus and are easily available in source and low in cost are still lacking. Moreover, few medicaments can simultaneously achieve the therapeutic and prophylactic effects.

SUMMARY OF THE INVENTION

In order to overcome the defects in the prior art, in one aspect of the present invention, provided is use of a two-dimensional nanomaterial in the preparation of a medicament for treating or preventing a coronavirus-induced disease; the two-dimensional nanomaterial is selected from the group consisting of copper indium thiophosphate nanosheet, graphene oxide nanosheet, molybdenum disulfide nanosheet, black phosphorus nanosheet and mixtures.

In the technical scheme of the present invention, the medicament in the above use further comprises a pharmaceutically acceptable carrier or excipient.

In the technical scheme of the present invention, the medicament in the above use further comprises a therapeutically effective amount of at least one of other administered therapeutic agents or a composition thereof selected from a corticosteroid, an anti-inflammatory signal transduction modulating agent, a β2-adrenoceptor agonist, a bronchodilator, an anticholinergic medicament, a mucolytic agent, hypertonic saline, and other medicaments for the treatment of Coronaviridae virus infection; or a mixture thereof.

In a second aspect of the present invention, provided is a pharmaceutical composition for treating or preventing a coronavirus-induced disease, comprising a two-dimensional nanomaterial as an active ingredient, the two-dimensional nanomaterial is selected from the group consisting of copper indium thiophosphate nanosheets, graphene oxide nanosheets, molybdenum disulfide nanosheets, black phosphorus nanosheets and mixtures.

In the technical scheme of the present invention, the above pharmaceutical composition further comprises a pharmaceutically acceptable carrier or excipient.

In the technical scheme of the present invention, the above pharmaceutical composition further comprises a second active ingredient selected from corticosteroids, anti-inflammatory signal transduction modulating agents, β2-adrenoceptor agonists, bronchodilators, anticholinergic medicaments, mucolytic agents, hypertonic saline, and other medicaments for the treatment of Coronaviridae virus infection; or a mixture thereof.

In the technical scheme of the present invention, the above pharmaceutical composition is in a formulation form selected from an oral formulation, an injection formulation, a mucosal administration formulation, an inhalant formulation, and an external formulation.

In a third aspect of the present invention, provided is a method for treating or preventing coronavirus infection, comprising administering to a subject a therapeutically effective amount of a two-dimensional nanomaterial, wherein the two-dimensional nanomaterial is selected from the group consisting of copper indium thiophosphate nanosheets, graphene oxide nanosheets, molybdenum disulfide nanosheets, black phosphorus nanosheets and mixtures.

In the technical scheme of the present invention, the therapeutically effective amount of the two-dimensional nanomaterial in the above method is administered in a formulation form, and the formulation further comprises a pharmaceutically acceptable carrier or excipient.

In the technical scheme of the present invention, the above method further comprises the step of administering to a subject a therapeutically effective amount of a second active ingredient selected from corticosteroids, anti-inflammatory signal transduction modulating agents, β2-adrenoceptor agonists, bronchodilators, anticholinergic medicaments, mucolytic agents, hypertonic saline, and other medicaments for the treatment of Coronaviridae virus infection; or a mixture thereof.

In a fourth aspect of the present invention, provided is use of a two-dimensional nanomaterial in the preparation of a formulation for inhibiting or reducing binding of a spike protein of a coronavirus or SARS-CoV-2 virus to a receptor ACE2 of a host cell thereof; the two-dimensional nanomaterial is selected from the group consisting of copper indium thiophosphate nanosheets, graphene oxide nanosheets, molybdenum disulfide nanosheets, black phosphorus nanosheets and mixtures; preferably, the two-dimensional nanomaterial inhibits the binding of the spike protein of the coronavirus to the receptor ACE2 of the host cell thereof through competitively binding to the RBD of the spike protein.

The present invention further provides use of a two-dimensional nanomaterial in the preparation of a formulation for competitively binding to the spike protein RBD of a coronavirus.

In a fifth aspect of the present invention, provided is use of a two-dimensional nanomaterial in the preparation of a medicament for facilitating the decomposition of a protein of SARS-CoV-2 virus; the two-dimensional nanomaterial is selected from the group consisting of copper indium thiophosphate nanosheets, graphene oxide nanosheets, molybdenum disulfide nanosheets, black phosphorus nanosheets and mixtures.

In the technical scheme of the present invention, use of a two-dimensional nanomaterial in the preparation of a medicament for facilitating the decomposition of the spike protein of the proteins of SARS-CoV-2 virus in the above method is further provided.

In a sixth aspect of the present invention, provided is use of a two-dimensional nanomaterial in the preparation of a medicament for facilitating the decomposition of RNA of SARS-CoV-2 virus; the two-dimensional nanomaterial is selected from the group consisting of copper indium thiophosphate nanosheets, graphene oxide nanosheets, molybdenum disulfide nanosheets, black phosphorus nanosheets and mixtures.

In a seventh aspect of the present invention, provided is use of a two-dimensional nanomaterial in the preparation of a material for inhibiting coronavirus infection; the two-dimensional nanomaterial is selected from the group consisting of copper indium thiophosphate nanosheets, graphene oxide nanosheets, molybdenum disulfide nanosheets, black phosphorus nanosheets and mixtures.

In an eighth aspect of the present invention, provided is a material for inhibiting coronavirus infection, comprising a two-dimensional nanomaterial and a matrix, wherein the two-dimensional nanomaterial is selected from the group consisting of copper indium thiophosphate nanosheets, graphene oxide nanosheets, molybdenum disulfide nanosheets, black phosphorus nanosheets and mixtures.

In the technical scheme of the present invention, the above material is a material used for preparing a protective article, and preferably, the protective article is a mask, a protective suit, a protective face mask, or a protective hat.

In the technical scheme of the present invention, the above material is a coating material.

In the technical scheme of the present invention, the above material is a disinfectant or a personal care article.

In the technical scheme of the present invention, the above material is a packaging material.

In the technical scheme of the present invention, the above material is a filtering material.

In a ninth aspect of the present invention, provided is an article comprising a two-dimensional nanomaterial, wherein the two-dimensional nanomaterial is selected from the group consisting of copper indium thiophosphate nanosheets, graphene oxide nanosheets, molybdenum disulfide nanosheets, black phosphorus nanosheets and mixtures;

the article is selected from a protective article, a coating material, a disinfectant, a personal care article, a packaging material, and a filtration device;

preferably, the protective article is a mask, a protective suit, a protective face mask, or a protective hat;

preferably, the coating material is a suspension comprising the two-dimensional nanomaterial, and the coating material can provide a coating having the two-dimensional nanomaterial on a surface of a coated object;

preferably, the disinfectant is an environmental disinfectant, a wash-free hand sanitizer, a hand sanitizer and a detergent; more preferably, the disinfectant is used for the surface disinfection of packaging materials, medical instruments, oral instruments and cosmetic instruments;

preferably, the packaging material is provided with a coating comprising the two-dimensional nanomaterial, or the packaging material is a composite material comprising the two-dimensional nanomaterial; more preferably, the packaging material is a packaging material used for medicaments or foods, in particular medicaments or food for cold chain transportation;

preferably, the filtration device is a device for air filtration, a device for water body filtration and a device for mask filtration; more preferably, the filtration device is an air filtering net, and a surface of the air filtering net is provided with the two-dimensional nanomaterial; more preferably, the filtration device is an air filtering cotton, and the two-dimensional nanomaterial is attached to the air filtering cotton fiber.

In the technical scheme of the present invention, the coronavirus is selected from one of HCoV-229E, HCoV-OC43, HCoV-NL63, HCoV-HKU1, SARS-CoV, SARS-CoV2, and MERS-CoV.

In the technical scheme of the present invention, the coronavirus is preferably selected from SARS-CoV, SARS-CoV2 and HCoV-NL63.

In the technical scheme of the present invention, the coronavirus is preferably selected from SARS-CoV and SARS-CoV2.

In the technical scheme of the present invention, the coronavirus-induced disease is a disease caused by coronavirus infection.

In the technical scheme of the present invention, the two-dimensional nanomaterial is a material with a length of nanometers in one dimension in space; preferably, a material with a length of 1-100 nm in one dimension in space, more preferably, a material with a length of 1-10 nm in one dimension in space, more preferably, a material with a length of 1-10 nm in one dimension and 100-500 nm in the other dimension in space, or, for example, 100 nm, 200 nm, 300 nm, 400 nm, or 500 nm in the other dimension.

In conclusion, compared with the prior art, the present invention has the following beneficial effects:

1. The two-dimensional nanomaterial such as the CIPS nanosheet, the graphene oxide nanosheet, the molybdenum disulfide nanosheet, or the black phosphorus nanosheet can inhibit the cell infection of coronavirus in one aspect, and can specifically adsorb and bind to coronavirus infection targets in another aspect, so that the infection efficiency of the virus is reduced, the replication of the virus in a host body is limited and the number of the coronavirus is reduced, thereby being used as a therapeutic medicament for patients with coronavirus.

2. The effect of CIPS in inhibiting SARS-CoV-2 virus infection is also suitable for SARS virus, which shows that CIPS has broad-spectrum property in inhibiting coronavirus.

3. The CIPS nanosheet, graphene oxide nanosheet, molybdenum disulfide nanosheet, or black phosphorus nanosheet can specifically bind to the coronavirus to inhibit the infection of SARS-CoV-2 virus on host cells, thereby achieving the specific adsorption and fixation of the virus. In addition to preparing medicaments, the two-dimensional nanomaterial can further be used for melt-blown cloth of a mask, a cold storage coating layer and an outer packaging coating layer or spraying agent, which can adsorb coronavirus and reduce the number of infectable viruses to better prevent novel coronavirus pneumonia.

4. The two-dimensional nanomaterial such as CIPS nanosheet has no influence on the survival rate of HEK-293T and Vero-E6 cells, and cannot cause haemolysis of red blood cells in mice, which indicates that the nanomaterial has high biological safety and low toxicity.

5. The two-dimensional nanomaterial of the present invention can be stored for a long time at a temperature between room temperature and $-20°$ C. and is convenient for storage. The two-dimensional nanomaterial of the present invention has high stability, and can be mixed and compounded with any auxiliary materials to prepare medicaments and composite materials, without being influenced by factors such as temperature, pH and the like.

6. The present invention adopts inorganic nanomaterial, which is diversified in material source, suitable for large-scale batch production, and low in cost and consumption.

7. The biolayer interferometry experiment of the present invention is conducted in solid and liquid environments, which demonstrates that CIPS can strongly bind to the Spike protein RBD of SARS-CoV-2 (SARS-CoV-2 RBD) (see FIG. 8). The results of the computer simulation also show that the binding occurs at 5.7 ns (FIG. 11). Moreover, the verification result in the embodiment of the present invention shows that the two-dimensional nanomaterial adopted herein was pre-incubated with coronavirus for 2 hours before conducting an evaluation of the infection experiment with the host cell, from which it can be found that the material of the present invention can bind to coronavirus for a long time and can be used for adsorbing coronavirus and preventing coronavirus from binding to the host cell. That is, the material of the present invention can instantaneously bind to coronavirus (for a long time), and can inhibit binding of virus to the host cell after the binding.

BRIEF DESCRIPTION OF THE DRAWINGS

In order to more clearly illustrate the technical schemes of the examples of the present invention, the drawings required to be used in the examples will be briefly described below. It should be understood that the following drawings only illustrate some examples of the present invention and therefore should not be considered as limiting the scope of the present invention, and those skilled in the art can also obtain other related drawings based on the drawings without creative efforts.

Figure 4:
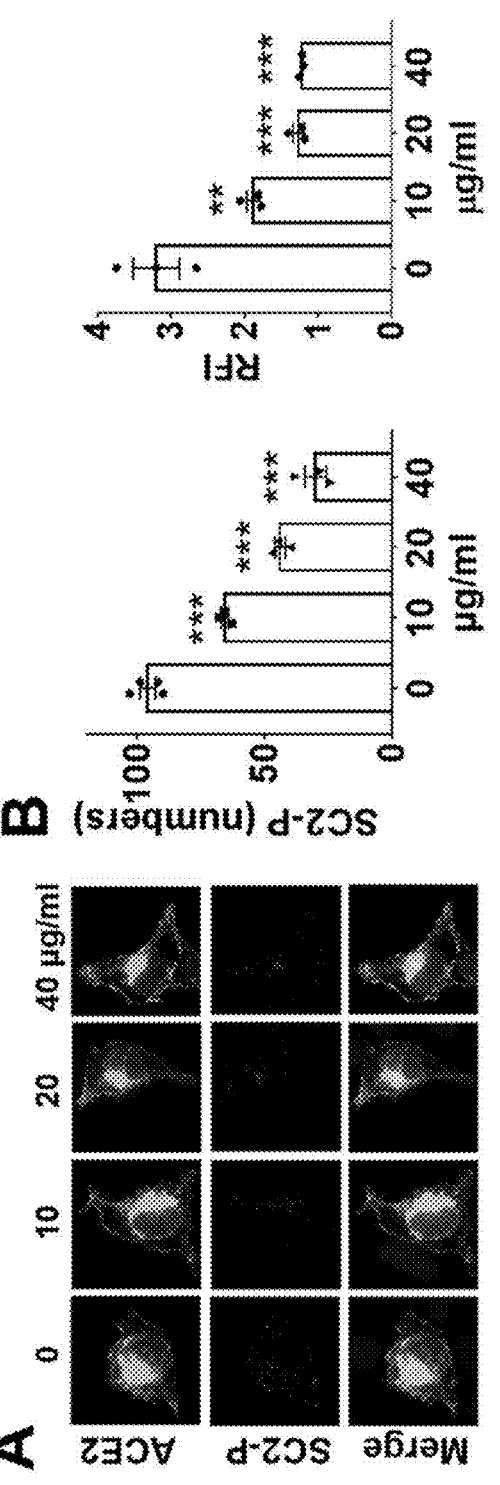
FIG. 4 shows the results of infection of 293T cells transfected with ACE2-GFP (ACE2/293T) by pseudovirus of spike protein of SARS-COV-2 (SC2-P) in the presence of CIPS nanosheets; ANOVA is used for statistical analysis, : $P<0.01$, *: $P<0.001$.

Wherein A of FIG. 4 shows the result of infection of ACE2/293T cells by SC2-P observed under a confocal microscope, line 1 (ACE2) represents ACE2/293T cell channel which is green fluorescent, line 2 (SC2-P) represents SC2-P channel which is red fluorescent; line 3 (Merge) is an overlap of line 1 and line 2, indicating the number and distribution of SC2-P entering ACE2/293T cells. The different columns in A of FIG. 4 represent different amounts of CIPS nanosheets, calculated as concentration after the CIPS nanosheets addition.

B of FIG. 4 shows the quantitative result of infection of ACE2/293T cells by SC2-P, wherein the abscissa of the left graph shows the amount of CIPS nanosheets added, calculated as concentration after the addition; the ordinate shows the number of SC2-P entering cells. The abscissa of the right graph shows the amount of CIPS nanosheets added, calculated as concentration after the addition; the ordinate shows the relative fluorescence intensity.

Figure 5:
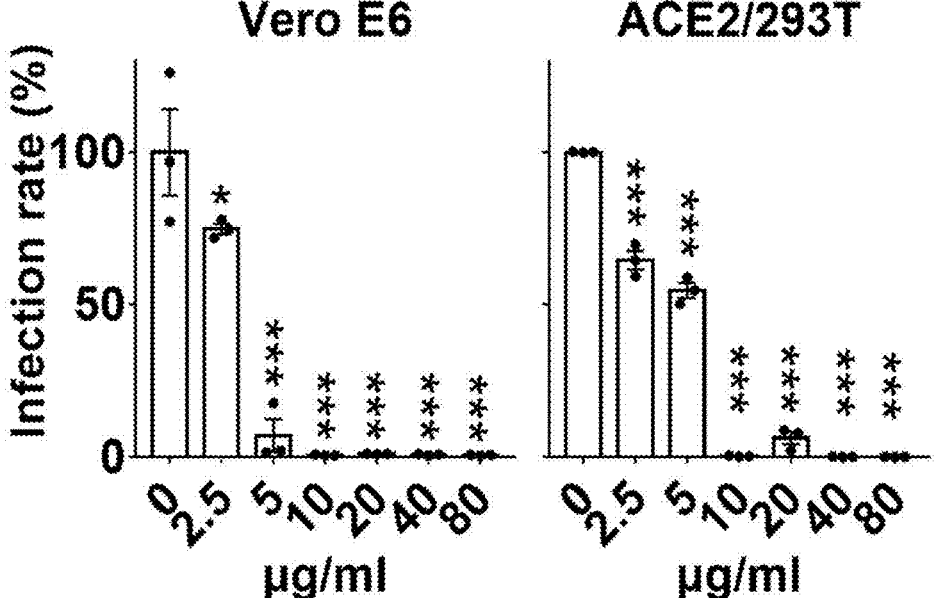
Figure 6:
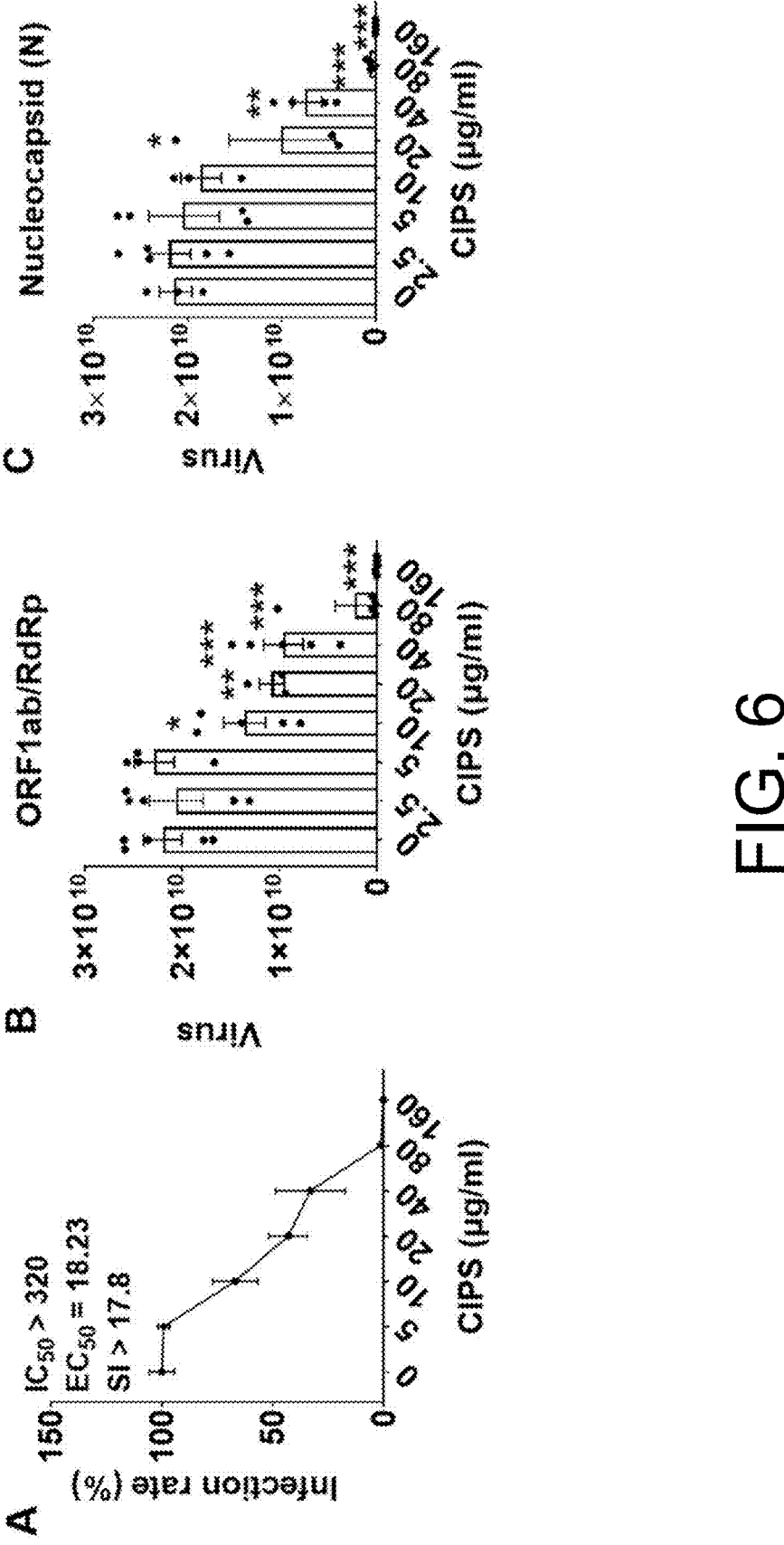
Figure 7:
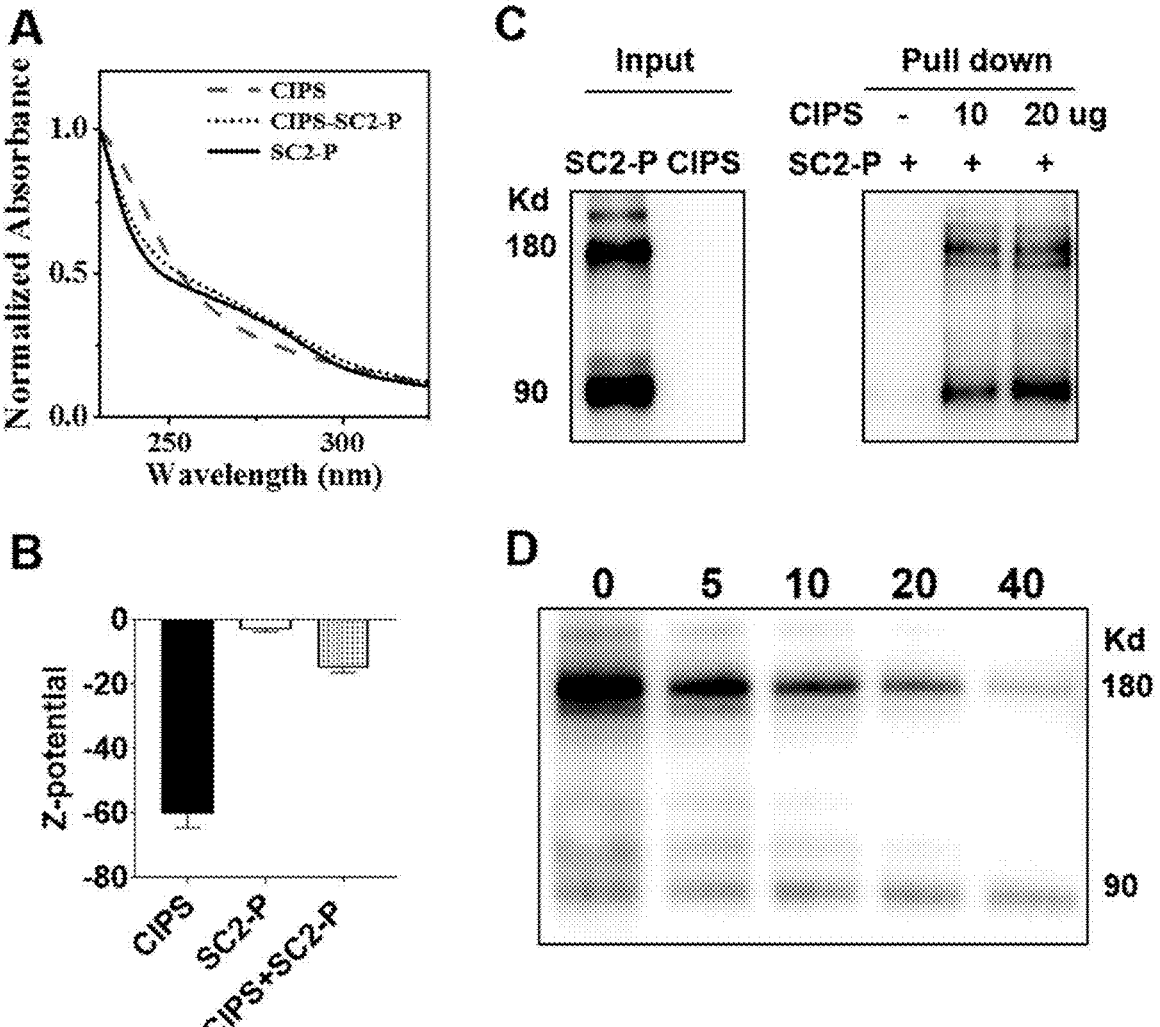
Figure 8:
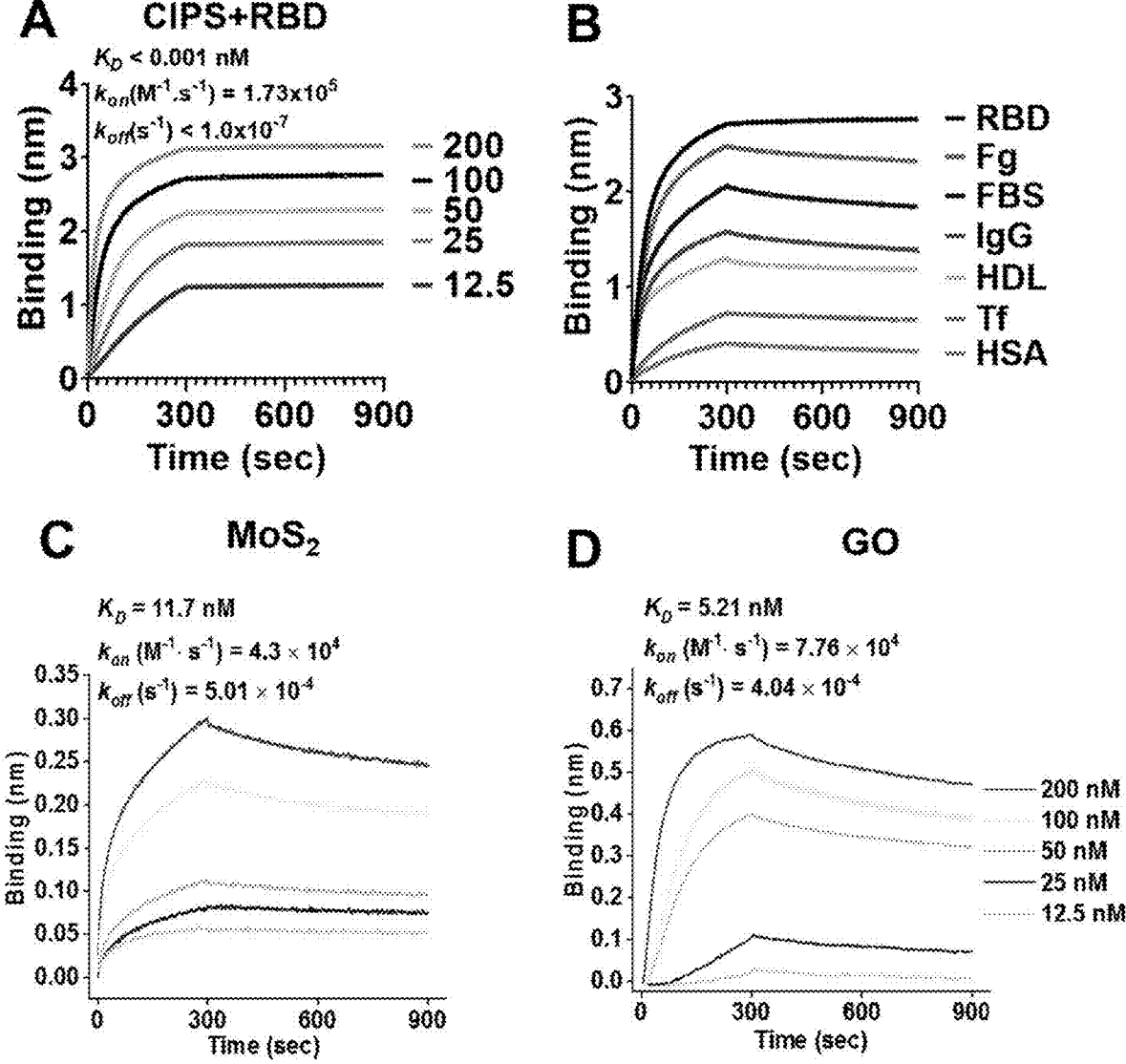

FIG. 5 shows the infection efficiency of pseudovirus SC2-P on Vero-E6 and ACE2/293T cells by detecting luciferase activity; ANOVA is used for statistical analysis, *: $P<0.05$, : $P<0.01$, *: $P<0.001$;

FIG. 6 shows the infection efficiency of novel coronavirus SARS-COV-2 on Vero-E6 cells by quantitative detection; ANOVA is used for statistical analysis, *: $P<0.05$, : $P<0.01$, *: $P<0.001$; A of FIG. 6 shows the infection rate of CIPS at different concentrations, B of FIG. 6 shows the amount of virus quantitatively detected with the expression amount of ORF1ab/RdRp gene as an index, and C of FIG. 6 shows the amount of virus quantitatively detected with the gene expression amount of nucleocapsid protein as an index;

FIG. 7 shows the CIPS adsorption and reduction of pseudovirus SC2-P;

FIG. 8 shows the results of quantitative determination of biolayer interferometry (BLI), wherein A of FIG. 8 shows the affinity of CIPS materials with different concentrations for the SARS-COV-2 RBD and the interaction therebetween; B of FIG. 8 shows the affinity of the CIPS materials for the protein in the serum and the interaction therebetween; C of FIG. 8 shows the affinity of molybdenum disulfide ($MoS_2$) nanosheets for SARS-COV-2 RBD and the interaction therebetween; D of FIG. 8 shows the affinity of graphene oxide (GO) nanosheets for the SARS-COV-2 RBD and the interaction therebetween; in the results of A, C and D of FIG. 8, the curves from top to bottom are respectively plotted at 200 nM, 100 nM, 50 nM, 25 nM and 12.5 nM in concentration; in the result of B of FIG. 8, the curves from top to bottom are respectively plotted at RBD, Fg, FBS, IgG, HDL, Tf and HAS.

Figure 9:
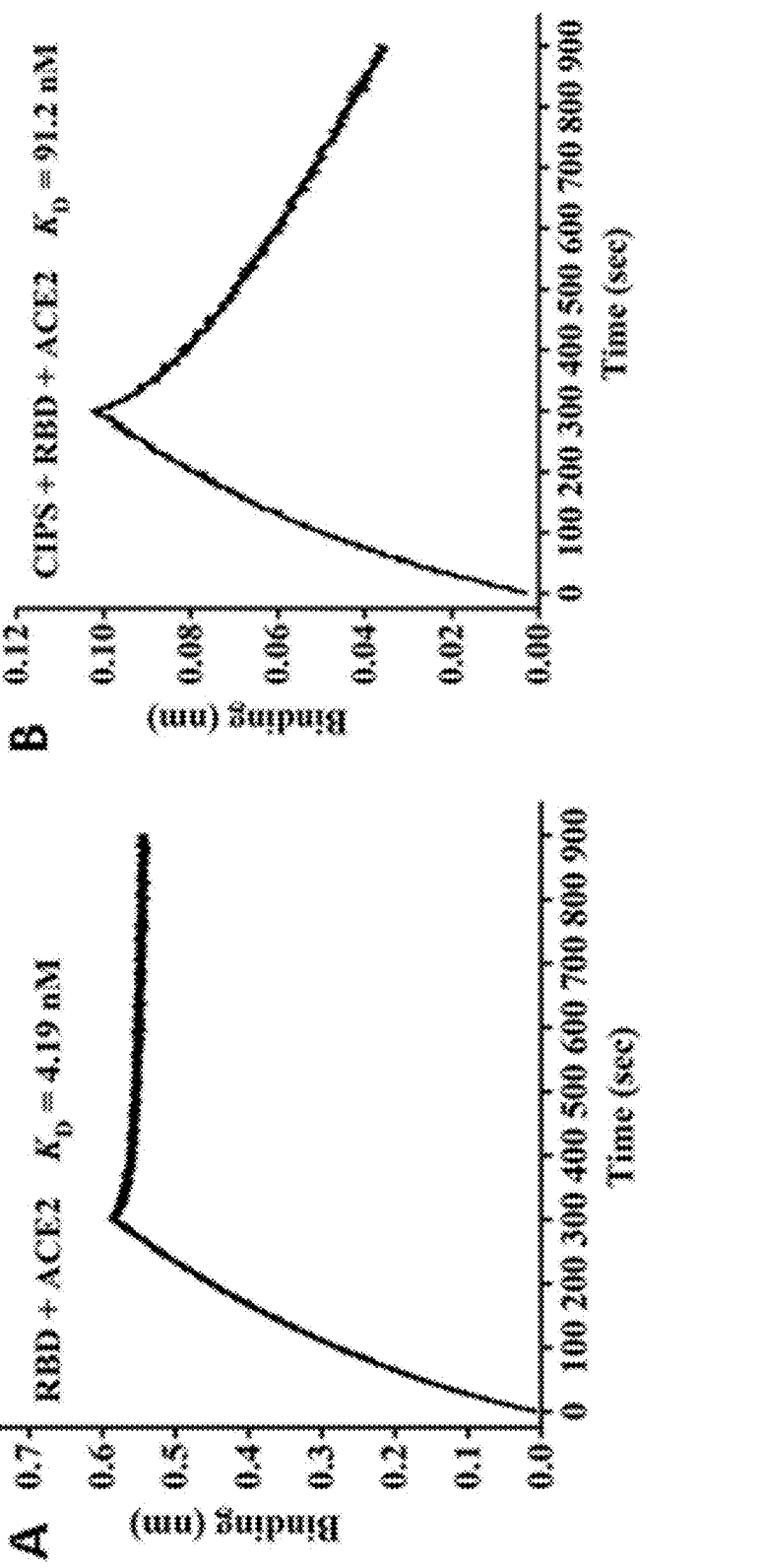
Figure 10:
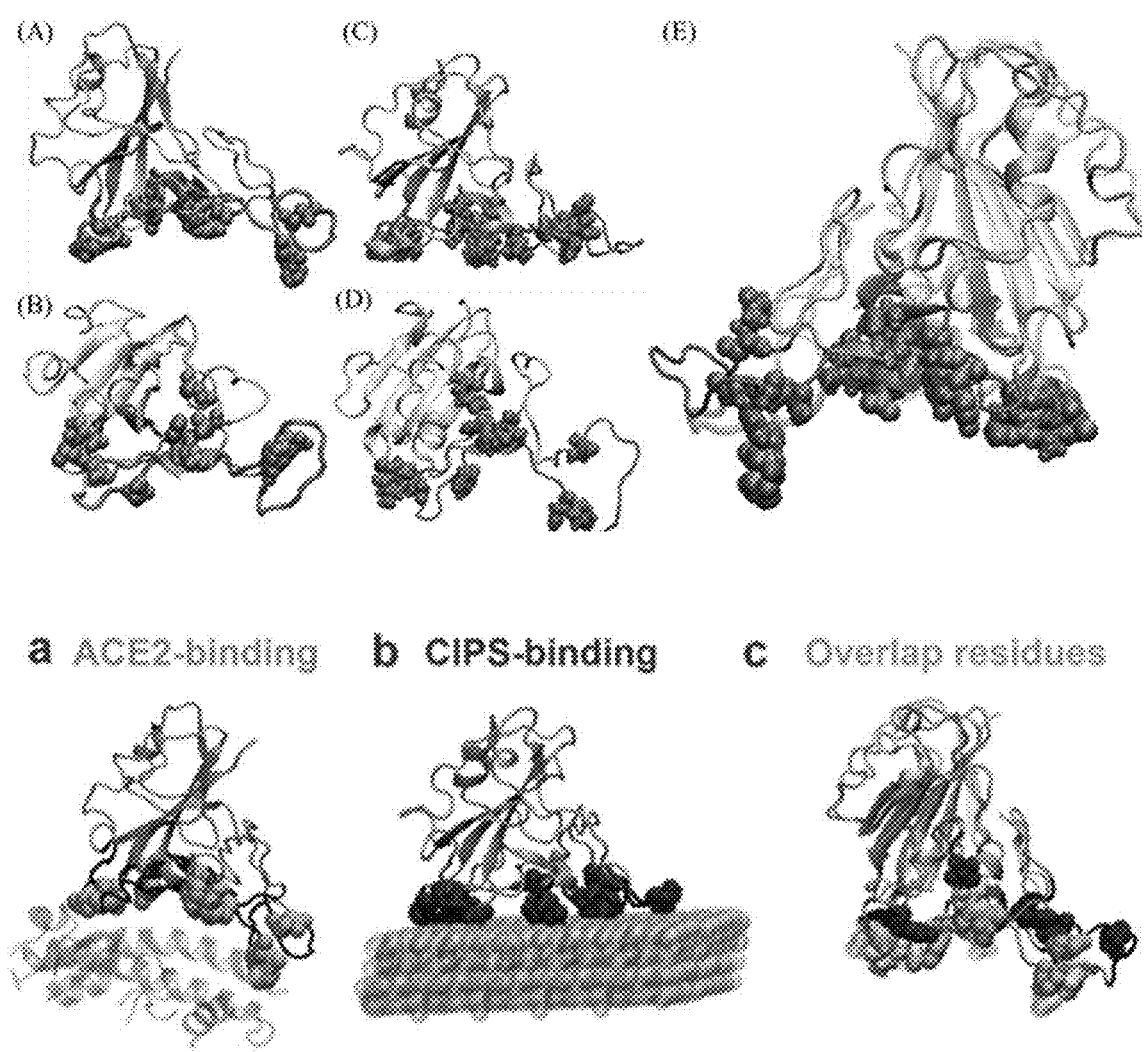
Figure 11:
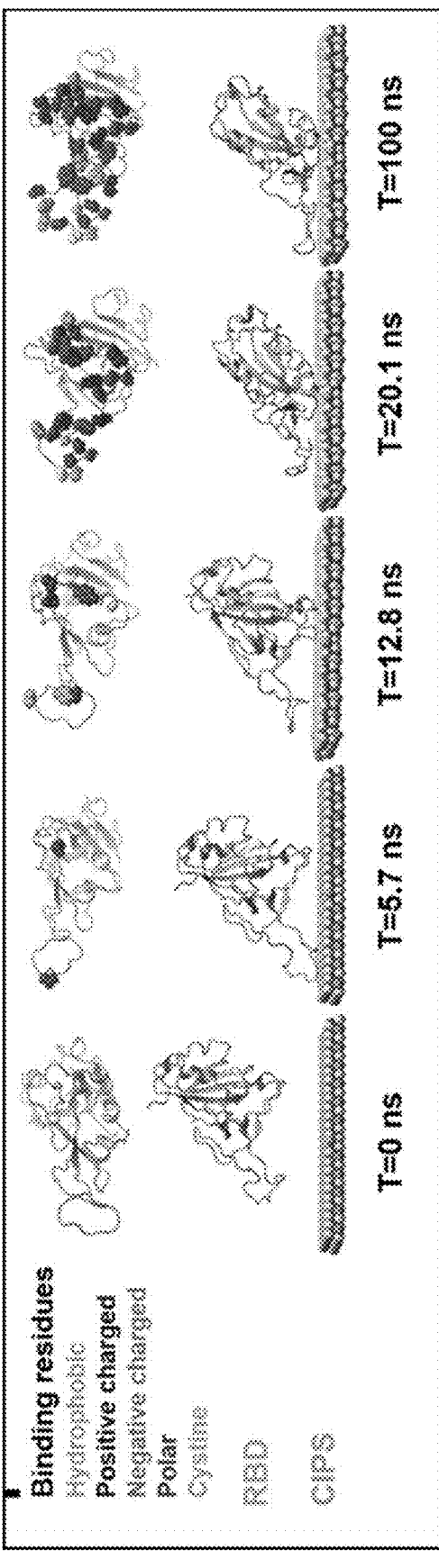

FIG. 9 shows the results of quantitative determination of biolayer interferometry (BLI) about the changes in the affinity of SARS-CoV-2 RBD for ACE2 protein before and after binding to CIPS;

FIG. 10 shows a mathematical model that simulates the binding of RBD to CIPS or ACE2;

FIG. 11 shows a mathematical model that simulates the binding of RBD to CIPS at different time points. The results of the computer simulation show that the binding occurs at 5.7 ns (binding time: 5.7 ns).

Figure 12:
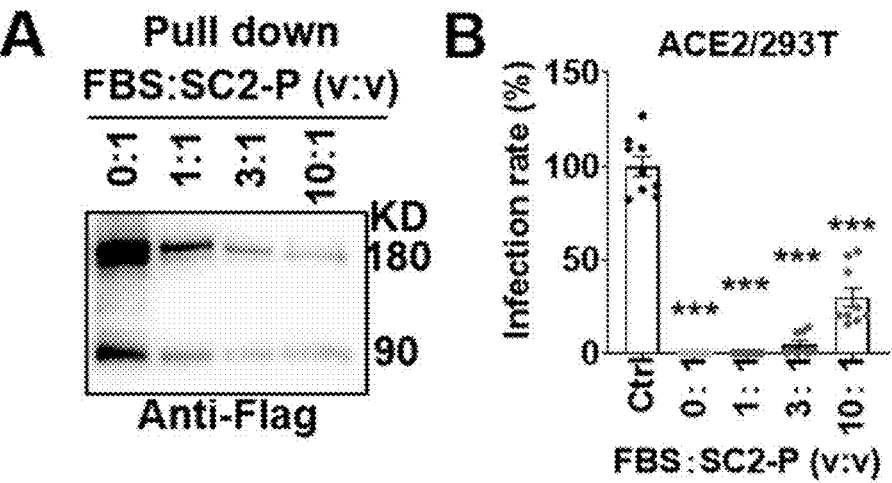

FIG. 12 shows the effects of CIPS in adsorbing and inhibiting the infection of SC2-P in a protein mixture solution with SC2-P and FBS. Wherein A of FIG. 12 shows that CIPS can bind to SC2-P in a protein mixture solution with SC2-P and 1, 3 or 10 times of the volume of FBS; B of FIG. 12 shows that CIPS can still inhibit the infection efficiency of SC2-P in a protein mixture solution.

Figure 13:
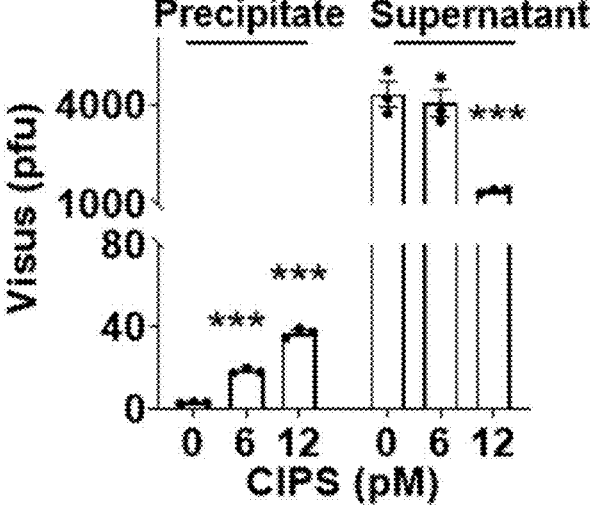

FIG. 13 is the result of Example 11, which shows the quantitative PCR result of CIPS adsorption of the euvirus SARS-CoV-2.

Figure 14:
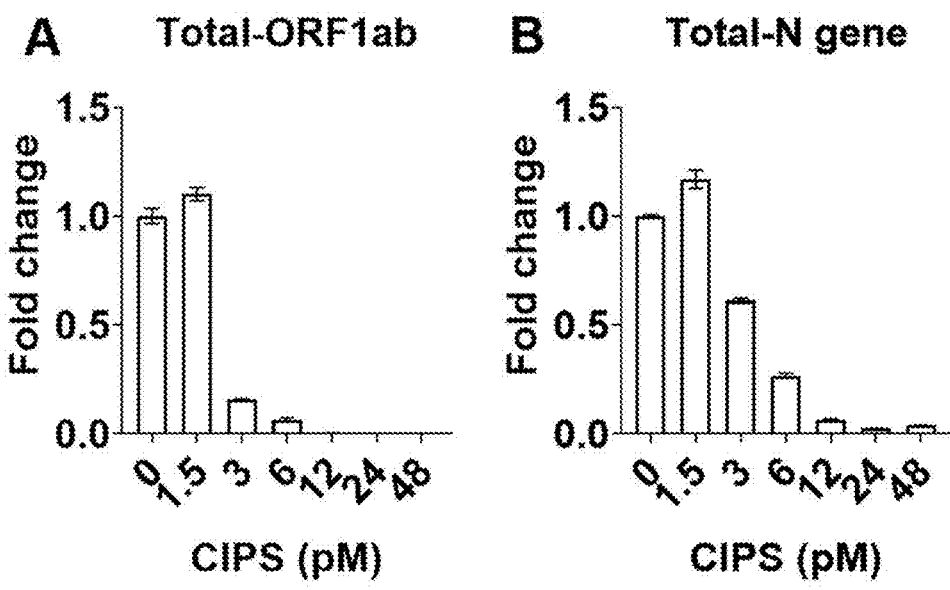

FIG. 14 is the results of Example 12, which shows that CIPS reduces the amount of the euvirus SARS-CoV-2.

Figure 15:
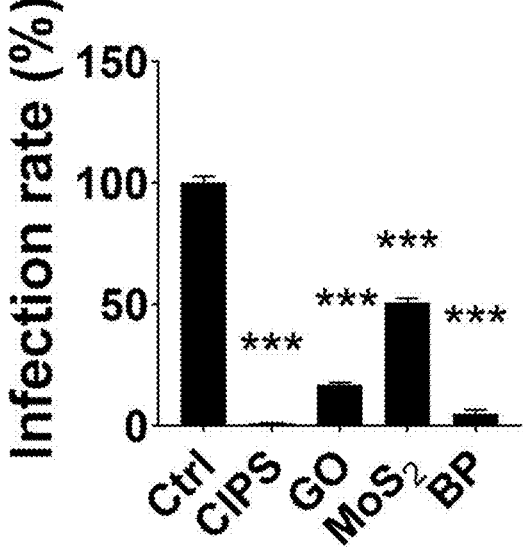

FIG. 15 shows the infection result of pseudovirus SC2-P on ACE2/293T cells in the presence of different two-dimensional nanomaterials, such as CIPS nanosheets, GO (graphene oxide) nanosheets, $MoS_2$ (molybdenum disulfide) nanosheets, or black phosphorus nanosheets.

Figure 16:
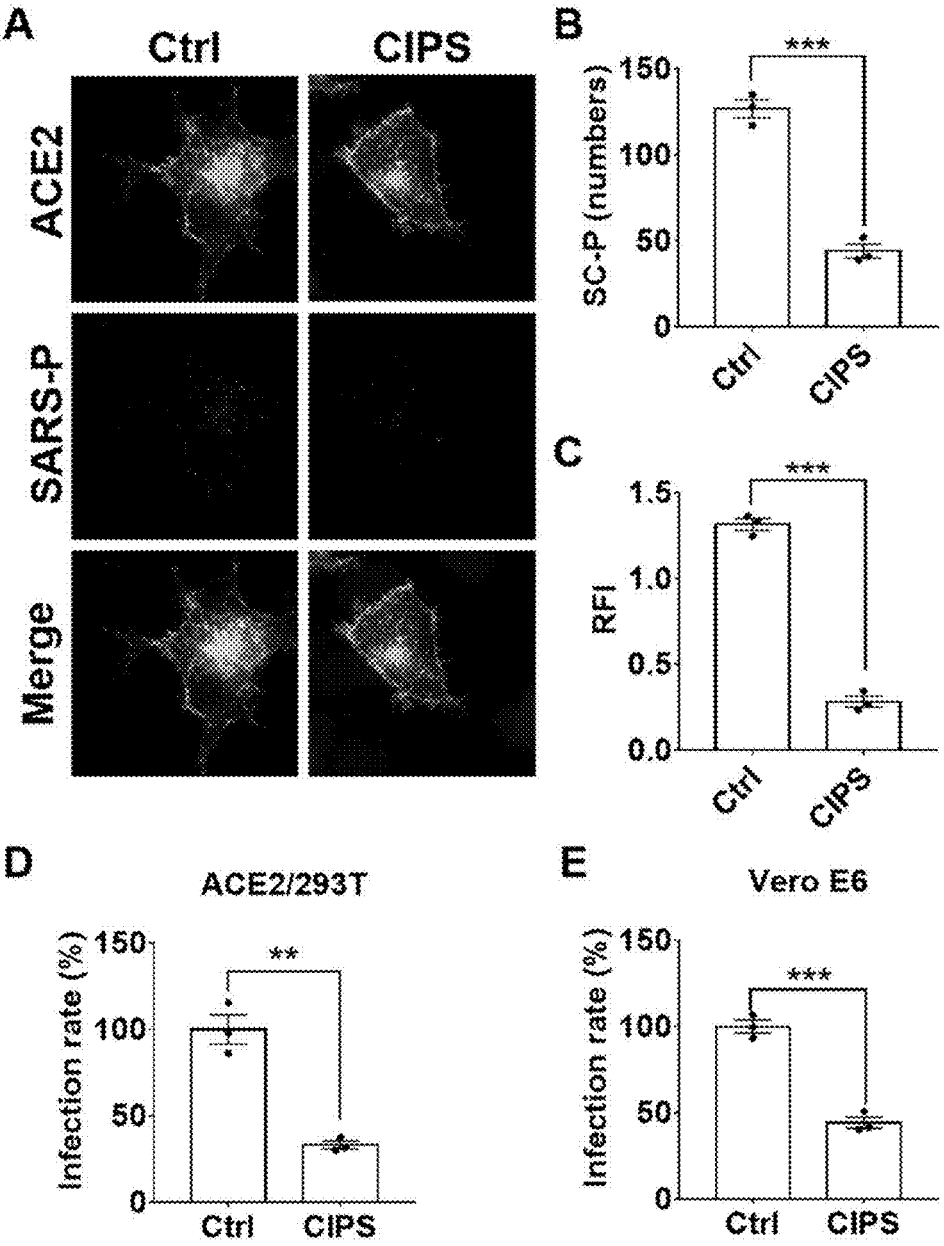

FIG. 16 shows the efficiency of CIPS in inhibiting the infection of SARS pseudovirus SARS-P.

DETAILED DESCRIPTION OF THE EMBODIMENTS

The technical schemes in the examples of the present invention will be clearly and completely described below with reference to the drawings in the examples of the present invention to help those skilled in the art better understand the schemes of the present invention, and it is obvious that the described examples are only a part of the examples of the present invention but not all of them. Based on the examples of the present invention, all other examples obtained by those of ordinary skill in the art without creative effort shall fall within the protection scope of the present invention.

The two-dimensional nanomaterials include graphene, transition metal disulfides, transition metal carbides, nitrides and carbonitrides, black phosphorus nanoplates, layered double hydroxides, two-dimensional MOFs, and other types of two-dimensional nanoplates, wherein the graphene oxide is a two-dimensional sp2 carbon atom layer containing an oxygen functional group, and is widely applied in the nanomedical field. Currently, no report is found that the two-dimensional nanomaterials, such as copper indium thiophosphate (CIPS) nanosheets, graphene oxide nanosheets, molybdenum disulfide nanosheets and black phosphorus nanosheets, have an effect on inhibiting the coronavirus infection, particularly cell infection of SARS virus and novel coronavirus SARS-CoV-2. The copper indium thiophosphate (CIPS) nanosheets, graphene oxide nanosheets, molybdenum disulfide nanosheets and black phosphorus nanosheets of the present invention have high biological safety and low toxicity, thereby being used in many fields such as medicine.

Terms

In the present invention, copper indium thiophosphate has the same meaning as CIPS or $CuInP_2S_6$.

In the present invention, the terms "nanosheet(s)" and "two-dimensional nanomaterial" have similar meanings and refer to a material with a nanoscale in one dimension in space, for example, a nanomaterial with a thickness of 1-100 nm. In the present invention, the two-dimensional nanomaterial is selected from any one or a combination of copper indium thiophosphate (CIPS) nanosheet, graphene oxide nanosheet, molybdenum disulfide nanosheet, and black phosphorus nanosheet. In a preferred embodiment, each two-dimensional nanomaterial is selected to be: the thickness (in one dimension in space) is 1-10 nm. The size of the nanosheet in the direction perpendicular to the thickness (in the other dimension in space) is 100-300 nm.

The "nanosheet(s)" can be obtained by stripping the obtained nanosheet materials by conventional methods in the art, for example, by mechanical grinding (e.g., ball grinding), sonication, and the like.

"Pharmaceutically acceptable carrier or excipient" includes, but is not limited to, any adjuvant, carrier, excipient, glidant, sweetener, diluent, preservative, dye/colorant, flavor enhancer, surfactant, wetting agent, dispersant, suspending agent, stabilizer, isotonic agent, solvent, or emulsifier that has been approved by Food and Drug Administration as the acceptable carrier or excipient for humans or livestock.

"Pharmaceutical composition" refers to a formulation of compounds of the present invention and vehicles widely accepted in the art for delivering biologically active compounds to mammals (e.g., humans). Such vehicles include all pharmaceutically acceptable excipients therefor.

"Effective amount" or "therapeutically effective amount" refers to an amount of compound according to the present invention which, when administered to a patient in need, is sufficient to treat a disease state, condition or disorder for which the two-dimensional nanomaterials have efficacy. Such an amount will be sufficient to elicit the biological or medical response in the tissue system or patient sought by the researchers or clinicians. The amount of the compound according to the present invention that constitutes a therapeutically effective amount will vary depending on such factors as: the compound and its biological activity, the composition used for administration, administration time, administration route, the rate of excretion of the compound, duration of treatment, type and severity of the disease state or condition being treated, the medicament administered in combination or in concert with the compound of the present invention, and the age, body weight, general health, sex, and diet of the patient. Such a therapeutically effective amount can be routinely determined by those of ordinary skill in the art based on their knowledge, the prior art, and the present disclosure.

Unless otherwise indicated, the term "treating" as used herein refers to reversing, alleviating, inhibiting the progression of, or preventing the disorder or condition to which such a term applies, or one or more symptoms of such disorder or condition. The term "treatment" as used herein refers to the act of treating, as "treating" is as defined immediately above. In some embodiments, the term "treating" is intended to mean administering the two-dimensional nanomaterials according to the present invention or a composition thereof to alleviate or eliminate symptoms of coronavirus infection and/or reduce viral loads in patients.

"Prevention" (prevention or preventing) refers to any treatment of a disease or condition that results in the failure of the clinical symptoms of the disease or condition to progress. The term "prevention" further includes administering a therapeutically effective amount of compound or composition according to the present invention prior to exposure of the individual to the virus (e.g., pre-exposure prevention) to prevent the onset of symptoms of the disease and/or to prevent the virus from reaching detectable levels in the blood.

The term "subject" or "patient" refers to an animal, such as a mammal (including a human), who has been or will be the object of treatment, observation or experiment. The methods described herein can be used in human treatment and/or veterinary applications. In some embodiments, the subject is a mammal (or patient). In some embodiments, the subject (or patient) is a human, a livestock animal (e.g., dogs and cats), a farm animal (e.g., cows, horses, sheep, goats, and pigs), and/or a laboratory animal (e.g., mice, rats, hamsters, guinea-pigs, pigs, rabbits, cats, dogs, and monkeys). In some embodiments, the subject (or patient) is a human. "Human (or patient) in need" refers to a human who may have or is suspected of having a disease or condition that would benefit from some treatment; for example, treatment with the two-dimensional nanomaterials disclosed herein or compositions thereof or pharmaceutical compositions containing the aforementioned ingredients according to the present invention.

Pharmaceutical Formulation

The two-dimensional nanomaterials of the present invention are formulated with conventional carriers and excipients selected in accordance with conventional practice. Tablets will comprise excipients, glidants, fillers, adhesives and the like. Aqueous formulations are prepared in sterile form, and are intended to be generally isotonic by delivery other than oral administration.

Although the active ingredient two-dimensional nanomaterials may be administered alone, it may be preferred to present them as pharmaceutical formulations. The formulations for veterinary and human use disclosed herein contain at least one active ingredient as defined above (the active ingredient is a two-dimensional nanomaterial: copper indium thiophosphate (CIPS) nanosheet, graphene oxide nanosheet, molybdenum disulfide nanosheet, and black phosphorus nanosheet, the same below) together with one or more acceptable carriers and other optionally therapeutic ingredients such as corticosteroids, anti-inflammatory signal transduction modulating agents, β2-adrenoceptor agonists, bronchodilators, anticholinergic medicaments, mucolytic agents, hypertonic saline, and other medicaments for the treatment of Coronaviridae virus infection; or a mixture thereof.

The formulations of the present invention suitable for oral administration may be presented as discrete units such as capsules, cachets or tablets each containing a predetermined amount of the active ingredient; as powders or granules; as a solution or suspension in an aqueous or non-aqueous liquid; or as an oil-in-water liquid emulsion or a water-in-oil liquid emulsion, or prepared into oral administration formulations by other known techniques.

Tablets are prepared by compression or molding, optionally with one or more additional ingredients. Compressed tablets may be prepared by compressing in a suitable machine the active ingredient in a free-flowing form such as powders or granules, optionally mixed with an adhesive, a lubricant, an inert diluent, a preservative, a surfactant or a dispersant. Molded tablets may be prepared by molding in a suitable machine a mixture of the powdered active ingredient moistened with an inert liquid diluent. The tablets may optionally be coated or nicked and optionally be formulated to provide slow or controlled release of the active ingredient therefrom.

The pharmaceutical composition of the present invention may be an external formulation such as an ointment for topical administration. For infections in the eyes or other external tissues such as the mouth and skin, the formulation is preferably a topical ointment or cream containing the active ingredient. When formulated into an ointment, the active ingredient may be employed with a paraffinic or a water-miscible ointment base. Alternatively, the active ingredient may be formulated into a cream with an oil-in-water cream base. If desired, the topical formulations may include compounds that accelerate the absorption or penetration of the active ingredient through the skin or other affected areas. Examples of such skin penetration accelerants include dimethyl sulfoxide and related analogs. The oil phase of the emulsion of the present invention may be constituted from known ingredients in a known manner. The oily phase may comprise only emulsifiers, but may also comprise mixtures of at least one emulsifier with a fat or an oil or with both a fat and an oil. Preferably, a hydrophilic emulsifier and a lipophilic emulsifier which acts as a stabilizer are included. Oil and fat are also preferably included.

The pharmaceutical composition of the present invention may be in the form of a sterile injection formulation, for example, a sterile aqueous or oleaginous suspension for injection.

The pharmaceutical composition of the present invention may be a formulation suitable for topical administration to the eyes including eye drops, wherein the active ingredient is dissolved or suspended in a suitable carrier, particularly in an aqueous solvent for the active ingredient.

The pharmaceutical composition of the present invention may be a formulation suitable for topical administration in the mouth, including lozenges containing the active ingredient in a flavor base (usually sucrose and acacia or tragacanth); lozenges containing the active ingredient in an inert base such as gelatin and glycerol or sucrose and acacia; and mouthwashes containing the active ingredient in a suitable liquid carrier.

The pharmaceutical composition of the present invention may be a formulation suitable for rectal administration, which may be presented as a suppository with a suitable base containing, for example, cocoa butter or salicylate.

The pharmaceutical composition of the present invention may be a formulation suitable for intrapulmonary or intranasal administration typically having a particle size in the range of 0.1-500 μm, such as 0.5, 1, 30, 35 μm and the like, which is administered by rapid inhalation of the nasal passage or by oral inhalation to reach the alveoli. The active ingredients of the present invention have a size that can be used for intrapulmonary or intranasal administration, and can be used for intrapulmonary or intranasal administration, for example, inhalants.

The pharmaceutical composition of the present invention may be a formulation suitable for parenteral administration including sterile aqueous and non-aqueous injection solutions, which may comprise antioxidants, buffers, bacteriostats and solutes which render the formulation isotonic with the blood of the intended recipient; and sterile aqueous and non-aqueous suspensions which may comprise suspending agents and thickening agents.

The formulations of the pharmaceutical composition of the present invention are presented in unit-dose or multi-dose containers, for example, sealed ampoules and vials, and may be stored in a freeze-dried (lyophilized) condition requiring only the addition of the sterile liquid carrier (for example water for injection) immediately prior to use. Instant injection solutions and suspensions are prepared from sterile powders, granules and tablets of the kind described above. Preferred unit-dose formulations are those containing a daily dose or unit, a daily sub-dose, or an appropriate fraction thereof, as described above, of an active ingredient.

The pharmaceutical composition of the present invention may be a veterinary composition comprising at least one active ingredient as defined above and a veterinary carrier.

The compound of the present invention is used to provide a controlled release pharmaceutical formulation containing one or more of the active ingredients of the present invention as an active ingredient, wherein the release of the active ingredient is controlled and modulated to allow less frequent administration or to improve the pharmacokinetic or toxic features of a given active ingredient.

Combination Treatment

The medicament, pharmaceutical composition or active ingredient of the present invention is also used in combination with other active ingredients. For the treatment of coronavirus infection, the other active ingredients are active against coronavirus infection, particularly SARS or SARS-CoV-2 infection. Non-limiting examples of such other active therapeutic agents include corticosteroids, anti-inflammatory signal transduction modulating agents, β2-adrenoceptor agonists, bronchodilators, anticholinergic medicaments, mucolytic agents, hypertonic saline, and other medicaments for the treatment of Coronaviridae virus infection; or a mixture thereof.

The medicament, pharmaceutical composition or active ingredient of the present invention may also be administered to a patient simultaneously or sequentially in combination with one or more other active ingredients in a unit-dose form. The combination treatment may be administered as a simultaneous or sequential regimen. When administered sequentially, the combination may be given in two or more administrations.

Co-administration of the medicament, pharmaceutical composition or active ingredient of the present invention with one or more other active ingredients generally refers to the simultaneous or sequential administration of a compound of the present invention and one or more other active therapeutic agents such that a therapeutically effective amount of the medicament, pharmaceutical composition or active ingredient of the present invention and one or more other active ingredients are all present in the body of a patient.

Combination treatment can provide "synergy" and "synergistic effect", i.e., the effect obtained when used together is greater than the sum of the effects produced by the compounds used alone. When the active ingredients are: (1) co-formulated and administered or delivered simultaneously in a combination formulation; (2) delivered alternately or in parallel as separate formulations; or (3) administered by other schemes, a synergistic effect can be obtained.

Composite Material

One application scheme of the present invention provides use of a two-dimensional nanomaterial in the preparation of a material for inhibiting coronavirus infection; the two-dimensional nanomaterial is selected from the group consisting of copper indium thiophosphate (CIPS) nanosheets, graphene oxide nanosheets, molybdenum disulfide nanosheets, and black phosphorus nanosheets.

One application scheme of the present invention provides a material for inhibiting coronavirus infection, wherein the material comprises two-dimensional nanomaterials and a matrix, the two-dimensional nanomaterial is selected from the group consisting of copper indium thiophosphate nanosheets, graphene oxide nanosheets, molybdenum disulfide nanosheets, black phosphorus nanosheets and mixtures copper indium thiophosphate (CIPS) nanosheets, graphene oxide nanosheets, molybdenum disulfide nanosheets, and black phosphorus nanosheets and mixtures.

In the above schemes of the material for inhibiting coronavirus, the material can further comprise a matrix, the matrix can vary according to the usage. The two-dimensional nanomaterial of the present invention has high stability and can adapt to various matrixes, so the material of the corresponding matrix can be obtained according to the conventional method in the art, including but not limited to the following steps of compounding the two-dimensional nanomaterials with the matrix, adsorbing the two-dimensional nanomaterials on the surface of the matrix in an adsorption manner; or blending the two-dimensional nanomaterials with a matrix, and then curing the matrix to give the composite material.

In the technical scheme of the present invention, the above material is a material used for preparing a protective article, and preferably, the protective article is a mask, a protective suit, a protective face mask, or a protective hat.

In the technical scheme of the present invention, the above material is a coating material.

In the technical scheme of the present invention, the above material is a disinfectant.

In the technical scheme of the present invention, the above material is a packaging material.

In the technical scheme of the present invention, the above material is a filtering material.

In a specific and preferred embodiment, the material for inhibiting coronavirus infection is used for preparing masks, and the material is a fabric, and the surface or the inside of the fabric comprises the two-dimensional nanomaterials of the present invention. In a variable and preferred embodiment, the material for inhibiting the coronavirus infection is used for preparing masks, and the material is a non-woven fabric, preferably a spun-bonded non-woven fabric or a melt-blown non-woven fabric; the surface or the inside of the non-woven fabric comprises the two-dimensional nanomaterials of the present invention. The preparation method of the above materials can be a conventional method in the art, comprising compounding the two-dimensional nanomaterials with the matrix material. For example, the melt-blown material can be compounded with the two-dimensional nanomaterials before melt-blown spinning, and then a melt-blown can be conducted, or the obtained melt-blown cloth can be compounded with the two-dimensional nanomaterials.

In a specific and preferred embodiment, the material for inhibiting the coronavirus infection is a coating material which is a suspension comprising the two-dimensional nanomaterials. Preferably, the coating material further comprises at least one of a surfactant and a thickener. The coating material can provide the two-dimensional nanomaterials on the surface of an object, such as a packaging surface, a medical device surface, a cosmetic device surface and the like, so that a coating layer comprising the two-dimensional nanomaterials is formed on the surface of the object. In a specific embodiment, the coating material provides a coating having the two-dimensional nanomaterials on the surface of outer package or inner package of foods or medicaments, and preferably, the foods or medicaments need to be transported in a cold chain.

In a specific and preferred embodiment, the material for inhibiting the coronavirus infection is a disinfectant which is a suspension comprising the two-dimensional nanomaterials. In a specific and preferred embodiment, the disinfectant is an environmental disinfectant, a wash-free hand sanitizer, a hand sanitizer or a detergent. In a specific and preferred embodiment, the disinfectant can be used for the surface disinfection of packaging materials, medical instruments (e.g., catheters, injection needles, surgical instruments, surgical masks, and other medical devices), oral instruments (e.g., dentures, protective strips, fillers, palatal expanders), and cosmetic instruments (e.g., beauty instruments, orthopedic devices). In a specific and preferred embodiment, the concentration of the two-dimensional nanomaterials in the disinfectant is in the range of 1-1000 μg/mL, preferably 2.5-160 μg/mL, more preferably 20 μg/mL.

In a specific and preferred embodiment, the material for inhibiting the coronavirus infection is a packaging material which is used for medicaments or foods for cold chain transportation or storage. The surface of the packaging material has a coating layer comprising the two-dimensional nanomaterials, or the packaging material is a composite material comprising the two-dimensional nanomaterials.

In a specific and preferred embodiment, the material for inhibiting the coronavirus infection is a filtering material which is a material for air filtration, a material for water body filtration and a material for mask filtration. In a specific and preferred embodiment, the filtering material is an air filtering net, and the surface of the air filtering net is provided with the two-dimensional nanomaterials. In a specific and preferred embodiment, the filtering material is an air filtering cotton, and the two-dimensional nanomaterials are attached to the fiber of the air filtering cotton. For example, the filtering material can be used for any device or equipment requiring air filtration, such as air conditioner filtration, air purifier filtration, fresh air system filtration and the like. The scene of use is not limited to home, office, laboratory, factory, etc.

In the technical scheme of the present invention, the material in the above use is a solid, liquid or semisolid material.

In the technical scheme of the present invention, the liquid material in the above use is a coating material comprising the two-dimensional nanomaterials, a disinfectant comprising the two-dimensional nanomaterials, or a personal care article comprising the two-dimensional nanomaterials.

In the technical scheme of the present invention, the solid material in the above use is an instrument or a packaging material comprising the two-dimensional nanomaterials on the surface.

In the technical scheme of the present invention, the semisolid material in the above use is a gel comprising the two-dimensional nanomaterials.

In the following, the present invention verifies the effect of the nanomaterials copper indium thiophosphate (CIPS or $CuInP_2S_6$) nanosheets on cell survival rate through specific examples, the inhibition of the CIPS nanosheets, the graphene oxide nanosheets, the molybdenum disulfide nanosheets and the black phosphorus nanosheets on cell infection of SARS-CoV-2 virus, the adsorption effect of CIPS on the novel coronavirus pseudovirus SC2-P, the specific adsorption of CIPS on the RBD domain of the spike protein of novel coronavirus, and analyzes the effect of CIPS on ACE2 recognition upon adsorption to the RBD domain of the spike protein through mathematical simulation.

The experimental materials used in the following examples include: HEK-293T cells, ACE2/293T cells, Vero-E6 cells, SARS-CoV-2 pseudovirus SC2-P, SARS pseudovirus SARS-P. Materials, reagents, carriers, strains and the like used in the following examples are commercially available unless otherwise specified.

HEK-293T cell is a derivative strain of human embryonic kidney cell 293, and is a cell line derived from the human embryonic kidney cells. It is highly transfectable and easy to cultivate, is widely used in expressing and researching exogenous genes as a common cell strain, and becomes a powerful tool for researching gene functions for many researchers.

ACE2/293T refers to an expression of ACE2 in HEK-293T cells.

ACE2 is also known as ACEH and called angiotensin-converting enzyme 2. The protein encoded by the gene belongs to an angiotensin-converting enzyme family of dipeptidyl carboxydipeptidase and has considerable homology with human angiotensin-converting enzyme 1. The protein encoded by the gene is a functional receptor of the spike glycoprotein of the human coronaviruses SARS, SARS-CoV-2, and HCoV-NL63.

Vero-E6 cell is an African green monkey kidney cell line, is one of the verified cells capable of being infected by the novel coronavirus, and can be used as a cell host for culturing the novel coronavirus. For example, it can be used for determining the effect of a drug on the replication rate of the novel coronavirus, detecting the presence of the novel coronavirus or cultivating the novel coronavirus for research purposes.

SC2-P is a pseudovirus expressing the spike protein of the novel coronavirus SARS-CoV-2. Pseudoviruses are a class of chimeric virions, which express the recombinant glycoprotein of other viruses on the surface of a replication-defective virus (virus vector). Due to advantages such as biological safety and stability, the pseudoviruses have been widely applied in vaccine research and development, antibody neutralization research, functional experiment of simulation of virus infection in cells, and as positive references in detection kits, and the like.

The current SARS-CoV-2 related pseudovirus system has two main types: one is constructed by a lentivirus system, wherein a capsid protein of the lentivirus envelops ORF1a/b, N, E and other genes of SARS-CoV-2, and it can be used as a positive control in a nucleic acid detection kit. The other pseudovirus system utilizes the spike protein of SARS-CoV-2 to envelop Luciferase/GFP and other marker genes, for simulating virus infecting cells, detecting the expression of the marker genes, and researching the infection efficiency thereby.

The SC2-P used in the following examples may be ordered by GENEWIZ company.

SARS-P is a pseudovirus of SARS and is a commercial product, and will not be described herein.

Example 1 Preparation of CIPS Nanosheets

Figure 1:
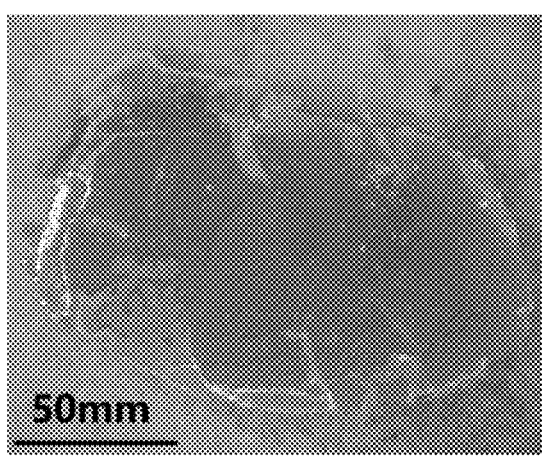
FIG. 1 shows an image of CIPS crystal plate.
Figure 2:
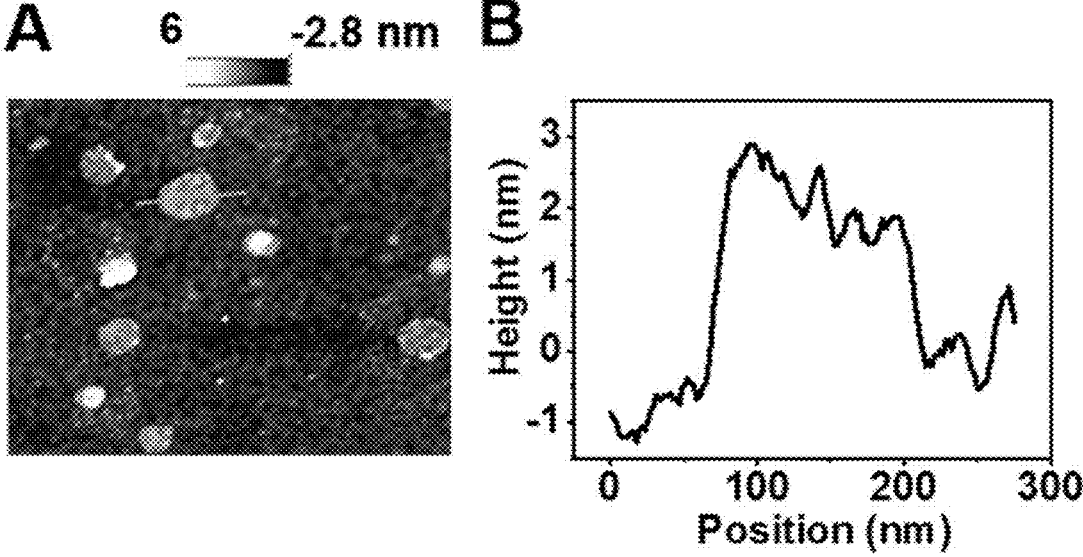
FIG. 2 shows atomic force microscope images of CIPS crystal plate.

CIPS single crystals were obtained by either purchase or known methods and subjected to mechanical grinding or other mechanical methods of stripping experiments to give CIPS nanosheets, as shown in FIG. 2, where the X-axis represents length and the Y-axis represents thickness, indicating a material thickness of about 1-10 nm. The size of the nanosheets in the direction perpendicular to the thickness is not uniform and ranges from 100 nm to 300 nm.

Example 2 Detection on the Biological Safety of CIPS Nanosheets

The specific procedures are as follows:

Vero-E6 cells and ACE2/293T cells were separately seeded onto 96-well plates at a density of $1 \times 10^4$ cells/well, and incubated at 37° C. and 5% $CO_2$ overnight.

The medium was changed to a medium comprising CIPS nanosheets at different concentrations (0, 2.5, 5, 10, 20, 40, 80, 160 μg/mL) and incubated at 37° C. for 24 h.

10 μL of CCK-8 solution was added into each hole according to the ratio of 1:10 and incubated for 30-60 min, and the absorbance value at 450 nm was determined.

The cell activity was calculated according to the following formula: cell activity=($A_{450}$ treatment group–$A_{450}$ blank group)/($A_{450}$ control group–$A_{450}$ blank group)×100%, wherein $A_{450}$ represents the absorbance value at 450 nm.

Figure 3:
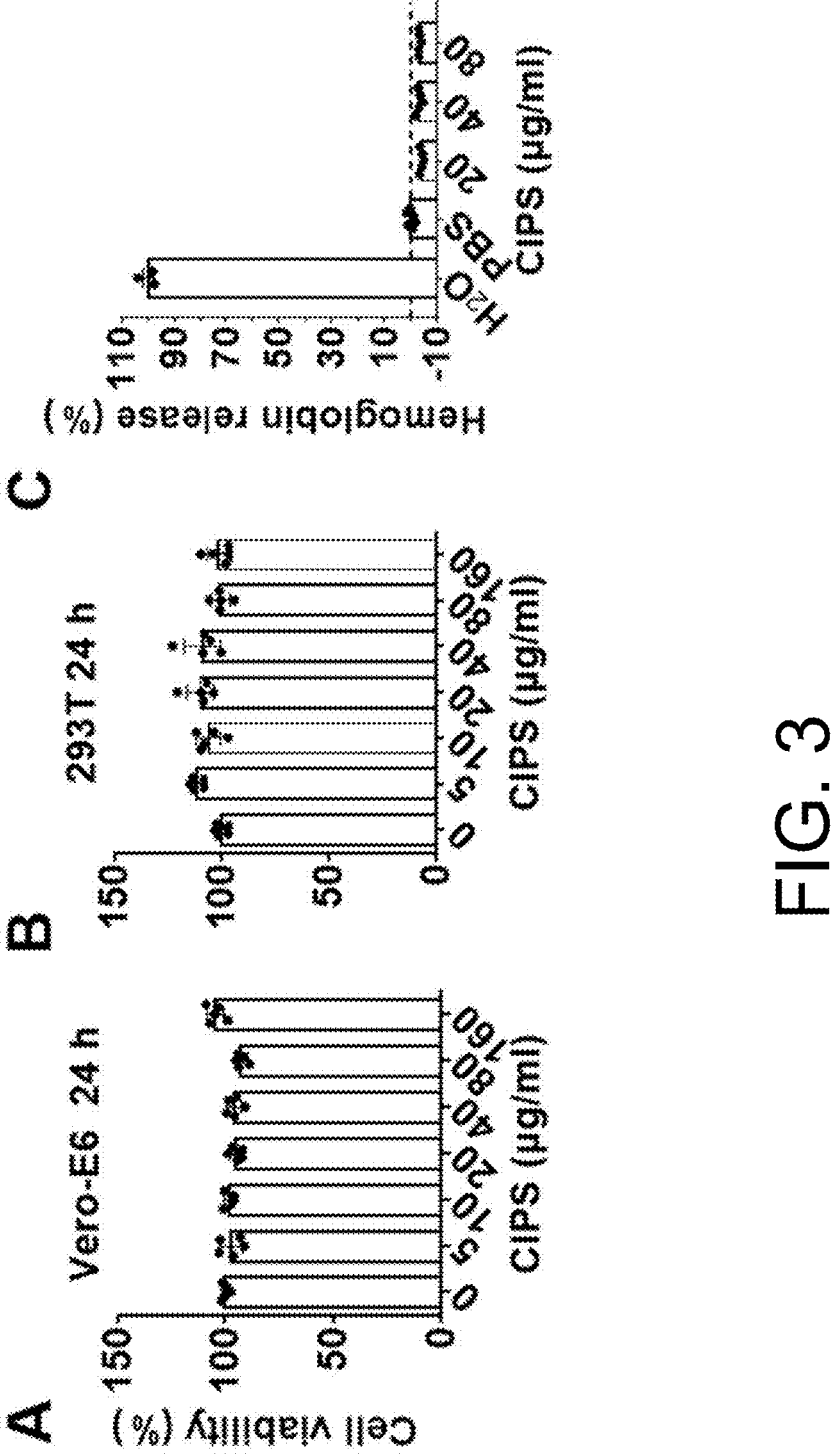
FIG. 3 shows biological safety detections of CIPS.

The result is shown in FIG. 3, and A of FIG. 3 shows detection of cell activity by CCK-8 after incubation of Vero-E6 cells with CIPS nanosheets at different concentrations (0-160 µg/mL) for 24 h. B of FIG. 3 shows detection of cell activity by CCK-8 after incubation of ACE2/293T cells with CIPS nanosheets at different concentrations (0-160 µg/mL) for 24 h. The result shows that the CIPS nanosheets at 0-160 µg/mL has no cytotoxicity to Vero-E6 and ACE2/293T cells, as the cell survival rate is not significantly reduced. The above result indicates that the CIPS nanosheets have better biocompatibility and high safety.

Blood was drawn through the orbit and 1 mL of fresh blood from healthy C57BL/6 mice was collected in an anticoagulation tube. The blood was centrifuged at 4° C. and 3000 rpm for 10 min. The upper serum was separated from the lower erythrocytes, and leucocytes and platelets on the surface layer of the erythrocytes were removed. The erythrocyte suspension was prepared by washing 3 times with pre-cooled PBS. 100 µL of 4% erythrocytes were added into an equal volume of CIPS nanosheets (40, 80, 160 µg/mL), and incubated at 37° C. for 4 h, and OD value at 540 nm was determined. The hemolysis rate was calculated by using purified water as a positive control (100% hemolysis) and PBS as a negative control (0% hemolysis). The formula is as follows: hemolysis index (Hem) $\% = (A_{sample} - A_{PBS})/(A_{purified\ water} - A_{PBS}) \times 100\%$, and the result shown in C of FIG. 3 indicates that the hemolysis rate of the CIPS nanosheets is 0, and the CIPS nanosheets have better biocompatibility and high safety.

Example 3 Immunofluorescence Detection of the Effect of CIPS Nanosheets on ACE2-GFP/HEK-293T Infection by SC2-P After placing a 14 mm cell slide in a 24-well plate, HEK-293T cells were seeded, incubated at 37° C. and 5% $CO_2$ overnight, and transfected with ACE2-GFP for 24 h. Then cells were infected with SC2-P mixed with the CIPS nanosheets of 0/10/20/40 µg/mL for 2 h, and the amount of the SC2-P infecting cells was detected by immunofluorescence. The specific procedures are as follows:

Cells on the cell slide on the 24-well plate were fixed with 4% paraformaldehyde at room temperature for 15 min and washed 3 times with PBS.

0.1% Triton X-100 was added for rupture of membranes for 15 min, and cells were washed 3 times with PBS.

Cells were blocked with 3% BSA in diluted PBS for 30 min, and washed 3 times with PBS.

Cells were incubated with Anti-Flag (rabbit origin 1:500) and Anti-GFP (mouse origin 1:500) for 2 h, and washed 3 times with PBS.

Then cells were incubated with 488 fluorescence-labeled mouse secondary antibodies and 555 fluorescence-labeled rabbit secondary antibodies for 1 h, washed 4 times with PBS, sealed by the anti-fluorescence quencher, and observed under a fluorescence confocal microscope.

The result is shown in A of FIG. 4, which is the result observed under a confocal microscope on the infection of ACE2-GFP/HEK-293T cells by SC2-P. After pre-incubation of SC2-P with CIPS nanosheets at different concentrations (0, 10, 20 and 40 µg/mL) for 2 h, ACE2-GFP/HEK-293T cells were infected, and infection of SC2-P was detected by immunofluorescence. B of FIG. 4 is ImageJ statistics of the number of SC2-P entering cells and fluorescence intensity. RFI represents the relative fluorescence intensity. The ACE2 channel is green fluorescent, the SC2-P channel is red fluorescent, and Merge is an overlap of the two, represented by grayscale. By observing the infection of SC2-P by immunofluorescence, SC2-P was observed to be able to enter into the host cell ACE2-GFP/HEK-293T, and the statistical result of B of FIG. 4 FIG. 4B also shows that the number of host cells into which SC2-P can enter and the fluorescence intensity were reduced in the treatment of CIPS nanosheets at different concentrations, and the degree of reduction was dose-dependent, wherein when the amount of CIPS nanosheets were only 10 µg/mL, a statistical difference was made from the negative control (i.e., the amount of CIPS nanosheets added were 0), and when the concentration reached 40 µg/mL, the infection was only 30% of the negative control. The above results indicate that the CIPS nanosheets can effectively inhibit SC2-P from entering into the host cells.

Example 4 Detection of the Effect of CIPS Nanosheets on Vero-E6 and ACE2/293T Infection by SC2-P with Luciferase Reporter Gene Vero-E6 cells and ACE2/293T cells were separately seeded onto 96-well plates at a density of $1 \times 10^4$ cells/well, and incubated at 37° C. and 5% $CO_2$ overnight.

Cells were infected by SC2-P mixed with CIPS nanosheets of 0/2.5/5/10/20/40/80 µg/mL for 2 h, respectively, washed once with DMEM, added with DMED medium and incubated for 40-48 h, and then luciferase activity was detected.

The results of the luciferase activity detection in FIG. 5 show that SC2-P can integrate the genome into the host cell. When the CIPS nanosheets were applied in treatment, the amount of Vero-E6 cells and ACE2/293T cells infected by SC2-P was significantly reduced compared with the control, and the degree of reduction was also dose-dependent. The above results show that the CIPS nanosheets can effectively inhibit SC2-P from infecting host cells.

Example 5 Detection of Inhibition of SARS-CoV-2 Euvirus Infection in Cells by CIPS Nanosheets Meanwhile, the present invention utilizes the euvirus SARS-CoV-2 to detect infection experiments, and similar results are obtained. Vero-E6 cells were infected by SARS-CoV-2 virus mixed with CIPS nanosheets of 0/2.5/5/10/20/40/80/160 µg/mL for 1 h respectively, and the amount of virus in the medium was quantitatively detected after 48 h. As shown in FIG. 6, the infection efficiency of the euvirus SARS-CoV-2 gradually decreased with increasing concentration of CIPS nanosheets. It demonstrates that the CIPS nanosheets can effectively inhibit infection of SC2-P on host cells and can also inhibit infection of the novel coronavirus SARS-CoV-2. A of FIG. 6 shows the infection rate of CIPS at different concentrations, B of FIG. 6 shows the virus amount quantitatively detected with the expression amount of ORF1ab/RdRp gene as an index, and C of FIG. 6 shows the virus amount quantitatively detected with the gene expression amount of nucleocapsid protein as an index.

Example 6 Characterization of the Physicochemical Property of CIPS Nanosheets: Adsorption of SC2-P by CIPS The binding capacity of the CIPS nanosheets to SC2-P was detected. The CIPS nanosheets and SC2-P were incubated together for 2 h to obtain a CIPS-SC2-P suspension, and the UV-VIS and Z-potential characteristics of the CIPS-SC2-P suspension, suspension of CIPS nanosheets alone and SC2-P suspension were separately detected. The results are shown in A to B of FIG. 7. A of FIG. 7 is the UV-VIS results of the CIPS-SC2-P suspension, suspension of CIPS nanosheets alone and SC2-P suspension, and it can be seen that the absorption peaks of CIPS and SC2-P are different, whereas the absorption peak of the CIPS-SC2-P suspension after 2 h incubation is shifted and the absorption intensity is changed with respect to the absorption peaks of the suspension of CIPS nanosheets alone and SC2-P suspension. B of FIG. 7 is the Z-potentials of the CIPS-SC2-P suspension, suspension of CIPS nanosheets alone, and SC2-P suspension, wherein the CIPS result is the Z-potential of the suspension of CIPS nanosheets alone, the SC2-P result is the Z-potential of the SC2-P suspension, and the CIPS+SC2-P result is the Z-potential of the CIPS-SC2-P suspension. The results show that the CIPS nanosheets can adsorb SC2-P.

Example 7 Detection of Adsorption and Reduction of SC2-P by CIPS Nanosheets by Western Blot Firstly, the CIPS nanosheets and the SC2-P were directly detected by Western blot separately, the result is shown in the left picture of C of FIG. 7, the protein in SC2-P can be clearly displayed in the result of the Western blot, whereas the protein in the CIPS nanosheets do not have the corresponding band display because the protein is absent. Then 0 µg, 10 µg and 20 µg of CIPS nanosheets were separately added into the SC2-P suspension, the mixture was incubated for 120 min and then was separated by centrifugation at the same speed, and the detection result by the Western blot is shown in the right picture of C of FIG. 7. The result of column 1 is the suspension comprising SC2-P alone, the Western blot does not have any band because the virus is too small to be separated by the centrifugation method, column 2 and column 3 are the results of 10 µg and 20 µg of CIPS nanosheets respectively. The CIPS nanosheets have an adsorption effect on SC2-P, so the CIPS nanosheets can be obtained by centrifugation, and has a corresponding band displayed in Western blot, the adsorption capacity can be increased with the increase of the adding amount of the CIPS nanosheets.

Meanwhile, SC2-P was incubated with different amounts of (0/5/10/20/40 µg) CIPS nanosheets for two hours, and the total amount of SC2-P was detected by Western blot. D of FIG. 7 shows that the amount of spike protein (the full length protein of 180 Kd) gradually decreased with the gradual increase of the amount of the CIPS nanosheets (D of FIG. 7), and it can be seen from the experimental results that CIPS nanosheets can facilitate the degradation of the full length protein spike of SC2-P and the amount of pseudovirus SC2-P decreased with the decomposition of the spike protein. This indicates that the CIPS nanosheets can not only adsorb SC2-P, but also reduce the amount of SC2-P.

Example 8 Competitive Binding of CIPS Nanosheets with ACE2 to Receptor Binding Domain (RBD) of Spike Protein of Novel Coronavirus SARS-CoV-2

The affinity of the CIPS nanosheets for the RBD domain of the spike protein of the novel coronavirus, proteins in serum and model protein BSA and interaction therebetween were quantitatively determined by biolayer interferometry (BLI). As shown in FIG. 8, KD values for different systems were calculated. The affinity of the CIPS nanosheets for the RBD domain of the S protein was proved to be strong, but the affinity for other proteins in serum was weak. This suggests the selective adsorption of RBD to CIPS nanosheets. This experiment demonstrates that the CIPS nanosheets can act on viruses separately and specifically bind to the RBD domain of the S protein of the virus. The experimental result shows that the CIPS nanosheets can be used before the binding to ACE2 protein and can be used for coronavirus prevention. In addition, $MoS_2$ and GO also have strong affinity for the RBD domain. This demonstrates that $MoS_2$ and GO nanosheets can also adsorb RBD, and experiments prove that the $MoS_2$ and GO nanosheets can each act on viruses independently and can specifically bind to the RBD domain of the S protein of the virus. The experimental result shows that both the $MoS_2$ and GO nanosheets can be used before the binding to ACE2 protein and can be used for coronavirus prevention.

In addition, the change in affinity of RBD protein for ACE2 protein before and after binding to CIPS nanosheets was quantitatively determined by biolayer interferometry (BLI). For interaction between RBD and ACE2: in 200 nM RBD protein solution, the sensor was chemically coupled and fixed with RBD protein for 300 s, and desorbed for 600 s; the sensor continued to adsorb for 600 s and desorb for 300 s in 100 nM ACE2 solution. The results show that the KD values of RBD and ACE2 are about 4 nM; FIG. 9 shows the KD value is 41 nM in the presence of CIPS nanosheets. This indicates that CIPS nanosheets resulted in a decrease in affinity of RBD for ACE2. This indicates that the CIPS nanosheets can reduce the binding of the spike protein of SARS-CoV-2 virus to the receptor ACE2 of the host cell thereof, thereby inhibiting the infection of the virus.

Based on the data obtained from the experiments, a mathematical model was used to simulate the binding of RBD to CIPS nanosheets or ACE2. FIG. 10 shows that the site of CIPS nanosheets binding to the RBD (A of FIG. 10) overlaps (C of FIG. 10) with the site of ACE2 binding to the RBD (B of FIG. 10). Moreover, the CIPS nanosheets have a stronger affinity for RBD than ACE2, so the CIPS nanosheets can competitively bind to RBD with ACE2. The CIPS nanosheets occupy a binding site of ACE2, so that the RBD is prevented from being bound to ACE2, and infection of a host cell by virus SARS-COV-2 can be inhibited. The abc at the lower part of FIG. 10 represent the binding sites for ACE2, the binding site for CIPS and the overlap of the two, respectively, and it can be seen from the overlap plot that the binding site for ACE2 overlaps with the binding site for CIPS.

Example 9 Simulation of Binding of RBD to CIPS and RBD Based on Molecular Dynamics (MD)

Typical trajectories of RBD and CIPS adsorption in a system were simulated based on Molecular Dynamics (MD). The bottom line shows the dynamic course of the RBD adsorption onto the surface of CIPS. The top line is a base map of RBD amino acid sites binding to CIPS, and VDW spheres are amino acid residues in contact with CIPS. The red balls are polar residues, the green color represents hydrophobic residues, the blue color represents positive charge residues, the purple color represents negative charge residues, and the yellow color represents cystine-containing disulfide bonds.

Example 10 Adsorption of SC2-P in a Protein Mixture Solution Containing SC2-P and FBS and Inhibition of Infection Efficiency of SC2-P by CIPS 1, 3 or 10 times of the SC2-P volume of FBS was mixed with SC2-P, respectively. After pre-incubation of the 20

µg/mL CIPS nanosheets with the protein mixture solution for 2 h, PBS was supplemented to 1 mL, and centrifugation was performed at 4000 rpm for 5 min. The amount of SC2-P in the precipitate was detected by WB. The results show that the CIPS can still adsorb SC2-P in the protein mixture solution.

1, 3 or 10 times of the SC2-P volume of FBS was mixed with SC2-P, respectively. After pre-incubation of 20 µg/mL CIPS nanosheets with the protein mixture solution for 2 h, ACE2/293T cells were infected for 2 h, and infection efficiency of SARS-P on ACE2/293T cells was detected by luciferase activity. The results show that the CIPS can adsorb SC2-P and inhibit the infection efficiency of SC2-P in a complex protein liquid environment.

Example 11 Quantitative PCR Detection of Adsorption of Euvirus SARS-CoV-2 by CIPS Nanosheets After incubation of 6000 pfu/500 ml of euvirus SARS-CoV-2 with CIPS at different concentrations (6 and 12 pM) for 2 h in P3 laboratory, meeting the operating specifications of P3 laboratory, the supernatant and precipitate were obtained by centrifugation at 4000 rpm for 5 min. RNA of the virus in the supernatant and precipitate were extracted, and the amount of the virus was quantified by quantitative PCR. As shown in FIG. 13, the results show that CIPS can bind to the euvirus SARS-CoV-2, and the amount of virus bound to CIPS obtained by centrifugation gradually increased with the increase of the amount of CIPS, and the amount of virus remaining in the supernatant gradually decreased.

Example 12 Quantitative PCR Detection of Reduction of the Amount of Euvirus SARS-CoV-2 by CIPS Nanosheets After incubation of 6000 pfu/500 ml of euvirus SARS-CoV-2 with CIPS at different concentrations (1.5-48 pM) for 2 h in P3 laboratory, meeting the operating specifications of P3 laboratory, all viruses were collected, RNA of the viruses was extracted, and the amount of the viruses was quantified by quantitative PCR. FIG. 14 shows that the amount of virus RNA gradually decreased with the gradual increase of the amount of CIPS nanosheets, and it can be seen from the experimental results that CIPS nanosheets can reduce the amount of virus RNA. This indicates that the CIPS nanosheets can not only adsorb the euvirus SARS-CoV-2, but also reduce the amount of SARS-CoV-2.

Example 13 Results of Infection of ACE2/293T Cells by SC2-P in the Presence of CIPS Nanosheets, Graphene Oxide (GO) Nanosheets, Molybdenum Disulfide (MoS₂) Nanosheets and Black Phosphorus (BP) Nanosheets as Different Two-Dimensional Nanomaterials ACE2/293T cells were seeded onto 96-well plates at a density of $1 \times 10^4$ cells/well, and incubated at 37° C. and 5% $CO_2$ overnight.

Cells were infected by SC2-P mixed with 20 µg/mL of CIPS nanosheets, GO (graphene oxide) nanosheets, $MoS_2$ (molybdenum disulfide) nanosheets or black phosphorus nanosheets for 2 h, respectively, washed once with DMEM, added with DMED medium and incubated for 40-48 h, and then luciferase activity was detected.

The luciferase activity detection result in FIG. 15 shows that different two-dimensional nanomaterials have the ability to inhibit infection of host cells by the novel coronavirus pseudovirus SC2-P. Ctrl group is a control group only applying SC2-P without adding any nanosheets. When the CIPS nanosheets or black phosphorus nanosheets were applied in treatment, the amount of ACE2/293T cells infected by SC2-P was significantly reduced compared with the control, and when the GO (graphene oxide) nanosheets, and the $MoS_2$ (molybdenum disulfide) nanosheets were applied, the amount of ACE2/293T cells infected by SC2-P was also significantly reduced compared with the control, but the effect is not as significant as that of applying the CIPS nanosheets or the black phosphorus nanosheets. The CIPS nanosheets, GO nanosheets, $MoS_2$ nanosheets group or black phosphorus nanosheets have significant differences from the control group (Ctrl group). The above results show that the CIPS nanosheets, GO nanosheets and $MoS_2$ nanosheets can effectively inhibit SC2-P from infecting host cells, and the CIPS nanosheets have the optimal effect.

Example 14 Inhibition Effect of CIPS Nanosheets on Infection of SARS Pseudovirus Particle SARS-P: Broad-Spectrum of the Inhibition Effect of Coronavirus The present invention is to detect whether the inhibition is specific for infection of SARS-COV-2 virus or suitable for other coronaviruses. The present invention also detects the inhibition effect of the CIPS nanosheets on infection of SARS pseudovirus particle SARS-P. The results are shown in FIG. 16, ANOVA is used for statistical analysis,  represents P<0.01, * represents P<0.001. A of FIG. 16 shows the infection of ACE2-GFP/HEK-293T cells by SARS-P observed under a confocal microscope. After pre-incubation of SARS-P and 20 µg/mL of CIPS nanosheets for 2 h, ACE2-GFP/HEK-293T cells were infected for 2 h, and infection of SARS-P was detected by immunofluorescence. B to C of FIG. 16 are ImageJ statistics of the number of SARS-P entering cells and fluorescence intensity. RFI represents the relative fluorescence intensity. D to E of FIG. 16 show the detection of the infection efficiency of SARS-P on ACE2/293T and Vero-E6 cells by luciferase activity. After pre-incubation of SARS-P and 20 µg/mL of CIPS nanosheets for 2 h, Vero-E6 and ACE2/293T cells were infected for 2 h, and after 40 h, the infection efficiency of SARS-P was detected by luciferase activity. The CIPS nanosheets can also inhibit the infection of SARS-P. This demonstrates that inhibition effect of CIPS nanosheets on virus infection is not only against SARS-COV-2 virus, but also against coronaviruses in a broad spectrum.

The present invention provides a nanodrug for inhibiting cell infection by SARS-CoV-2 virus, wherein the nanodrug is any one or more of copper indium thiophosphate nanosheets, graphene oxide nanosheets and molybdenum disulfide nanosheets.

Embodiment 1: an oral liquid comprising any one or more of copper indium thiophosphate nanosheets, graphene oxide nanosheets, molybdenum disulfide nanosheets and black phosphorus nanosheets as the medicinal ingredient;

Taking oral liquid as an example, the oral liquid is a new dosage form developed based on decoction and injection, and it has the advantages of small dosage, quick absorption, stable quality, and is convenient to carry and administrate, and easy to store. It contains various effective ingredients which have great influence on quality and taste. On the premise of not changing the structure and the function of the main active ingredients, how to retain the effective ingredients to the maximum extent and improve the taste is a difficult point in selecting auxiliary material. The oral liquid can be added with auxiliary material to improve the taste, the clarity, the stability and the product quality.

The common auxiliary materials for the oral liquid comprise: solvent, aromatic, corrigent, clarifier, preservative, etc., and these auxiliary materials can be added simultaneously or optionally, wherein the solvent is essential and water can be used. The different combinations of auxiliary materials comprise sweetener, aromatic, clarifier or preservative, or the combination of sweetener and preservative, preferably the combination of sweetener and preservative. Part of the auxiliary materials have the functions of sweetening and flavoring, and only one auxiliary material needs to be added at the moment.

For the oral liquid, preferably, the sweetener is selected from one or more of aspartame, xylitol, aspartame and sucralose.

For the oral liquid, preferably, the preservative is selected from one or more of paraben, butylhydroxyanisole, butylhydroxytoluene and sorbic acid.

The preservative can be selected from paraben, butylhydroxytoluene and sorbic acid, preferably butylhydroxytoluene. Combinations may also be used, for example, the combination of paraben with butylhydroxytoluene, or the combination of butyl hydroxytoluene with sorbic acid, or the combination of paraben, butylhydroxytoluene and sorbic acid.

For the oral liquid, preferably, the aromatic is fruit essence.

For the oral liquid, preferably, the clarifier is one or a mixture of chitosan and gelatin.

Embodiment 2: a tablet comprising any one or more of copper indium thiophosphate nanosheets, graphene oxide nanosheets, molybdenum disulfide nanosheets and black phosphorus nanosheets as the medicinal ingredient;

The tablet has the advantages of accurate dosage, stable quality, and convenient administration, carrying and transportation, etc.

For the tablet, the formulation auxiliary material includes one or more of diluents, adhesives, lubricants and disintegrants, preferably a combination of diluents, adhesives, lubricants and disintegrants.

For the tablet, preferably, the diluent is one or more of cellulose and inorganic salts, such as microcrystalline cellulose, calcium sulfate, calcium hydrogen phosphate, medicinal calcium carbonate, mannitol, etc., to increase the volume of the raw materials and facilitate the shaping.

For the tablet, preferably, the adhesive is one or more of water, ethanol, sodium carboxymethylcellulose, hydroxypropylcellulose, methylcellulose, ethylcellulose, gelatin, polyvinylpyrrolidone, and the like.

For the tablet, preferably, the lubricant is one or more of magnesium stearate, aerosil, talc, hydrogenated vegetable oil, polyethylene glycol and magnesium lauryl sulfate.

For the tablet, preferably, the disintegrant is one or more of low-substituted hydroxypropyl, crospovidone, croscarmellose sodium and the like.

Embodiment 3: a capsule comprising any one or more of copper indium thiophosphate nanosheets, graphene oxide nanosheets, molybdenum disulfide nanosheets and black phosphorus nanosheets as the medicinal ingredient;

In the present invention, the capsule mainly improves the stability and bioavailability of the medicament. The formulation auxiliary material is a capsule shell, and the capsule shell is a hard capsule shell or a soft capsule shell.

Embodiment 4: a granule comprising any one or more of copper indium thiophosphate nanosheets, graphene oxide nanosheets, molybdenum disulfide nanosheets and black phosphorus nanosheets as the medicinal ingredient;

The granule can be directly swallowed, or be infused with warm water, and has advantages of convenient application and carrying, and rapid dissolution and absorption. The formulation auxiliary materials used in the granule are similar to those of the tablet, and relate to one or more of fillers, adhesives, wetting agents, disintegrants, lubricants and film coating materials.

For the granule, preferably, the filler is one or more of cellulose and inorganic salts. such as microcrystalline cellulose, calcium sulfate, calcium hydrogen phosphate, medicinal calcium carbonate, mannitol, etc., to increase the volume of the raw materials and facilitate the shaping.

For the granule, preferably, the adhesive is one or more of water, ethanol, sodium carboxymethylcellulose, hydroxypropylcellulose, methylcellulose, ethylcellulose, gelatin, polyvinylpyrrolidone, and the like.

For the granule, preferably, the wetting agent is water or ethanol or a mixture of both. For example, one or more of magnesium stearate, aerosil, talc, hydrogenated vegetable oil, polyethylene glycol and magnesium lauryl sulfate.

For the granule, preferably, the disintegrant is one or more of low-substituted hydroxypropyl, crospovidone, croscarmellose sodium and the like.

For the granule, preferably, the film coating material is one or more of hydroxypropyl methylcellulose, polyethylene glycol, cellulose acetate phthalate and polyvinyl acetal diethylamine acetate.

Embodiment 5: a dispersant comprising any one or more of copper indium thiophosphate nanosheets, graphene oxide nanosheets, molybdenum disulfide nanosheets and black phosphorus nanosheets as the medicinal ingredient.

The present invention can also be prepared into a dispersant which is convenient for dose distribution and administration.

Taking a beverage as an example, the composition of the present invention can be prepared into beverages with different flavors which will be popular as a daily drink.

The formulation auxiliary material used for the beverage comprises at least one of clarifier, preservative and flavoring agent.

The composition of the present invention can also be prepared into other dispersants, for example, functional milk powder, and the added auxiliary materials are mainly milk powder, such as skimmed milk powder and skimmed sugarfree milk powder.

In the above embodiments, the dose of the medicament in the unit product can be adjusted to adapt for different usages, such as medicines, health products, foods and the like.

In a preferred example of the present invention, provided is a melt-blown cloth of a mask for preventing cell infection by SARS-CoV-2 virus, wherein any one or more of copper indium thiophosphate nanosheets, graphene oxide nanosheets, molybdenum disulfide nanosheets and black phosphorus nanosheets are added to the melt-blown cloth of a mask.

In a preferred example of the present invention, provided is a cold storage coating layer or an outer packaging coating layer for inhibiting cell infection by SARS-CoV-2 virus, wherein any one or more of copper indium thiophosphate nanosheets, graphene oxide nanosheets, molybdenum disulfide nanosheets and black phosphorus nanosheets are added to the cold storage coating layer or the outer packaging layer.

In a preferred example of the present invention, provided is a disinfection spray for inhibiting cell infection by SARS-CoV-2 virus, wherein any one or more of copper indium thiophosphate nanosheets, graphene oxide nanosheets, molybdenum disulfide nanosheets and black phosphorus nanosheets are added to the spray. The spray further comprises a solvent which is water and has no toxicity besides any one or more of copper indium thiophosphate nanosheets, graphene oxide nanosheets, molybdenum disulfide nanosheets and black phosphorus nanosheets, wherein the effective concentration of the copper indium thiophosphate nanosheets, the graphene oxide nanosheets, the molybdenum disulfide nanosheets and the black phosphorus nanosheets is 2.5-160 μg/mL (as shown in FIG. 3), the inhibition effect is not significant at very low concentration, but the cost is increased when the concentration is high, which is not suitable for commercial production. The preferable concentration is 20 μg/mL.

In conclusion, the present invention verifies that the two-dimensional nanomaterials, CIPS nanosheets, graphene oxide nanosheets, molybdenum disulfide nanosheets and black phosphorus nanosheets, can inhibit the infection efficiency of SARS-CoV-2 virus. CIPS can also inhibit the infection of SARS-P. This indicates that inhibition effect of CIPS nanosheets on virus infection is not only against SARS-CoV-2 virus, but also against coronaviruses in a broad spectrum.

Taking CIPS as an example, the present invention also verifies the effect of CIPS on cell survival rate. The experimental result shows that CIPS (1-160 μg/mL) has no influence on the activity of Vero-E6 and ACE2/293T cells, and has no cell hemolysis, which indicates that it has high biological safety and low toxicity.

The present invention also verifies the inhibition of the CIPS on the infection efficiency of the SARS-CoV-2 virus. Experiments prove that CIPS inhibits the infection efficiency of pseudovirus (SC2-P) of SARS-CoV-2 to ACE2-GFP/HEK-293T (ACE2-GFP is expressed in HEK-293T) and Vero-E6. Experiments also prove that the CIPS can inhibit the infection efficiency of the euvirus SARS-CoV-2 to Vero-E6.

The present invention also verifies the adsorption effect of the CIPS on the SC2-P. Experiments prove that the CIPS can adsorb and reduce SC2-P. And the CIPS has stronger binding effect on the receptor binding domain (RBD) of the spike protein of SARS-CoV-2 virus compared with other proteins, and the CIPS can inhibit the binding of the virus to its receptor.

Therefore, the nanomaterial of the present invention can be prepared into nanodrugs for treating the novel coronavirus pneumonia, or can be added into melt-blown cloth of a mask, a cold storage coating layer, an outer packaging coating layer and a spray to inhibit the propagation of the novel coronavirus pneumonia, so that the prevention effect is achieved. The inhibition effect of the two-dimensional nanomaterial of the present invention on virus infection is not only against SARS-CoV-2 virus, but also against coronaviruses in a broad spectrum. The two-dimensional nanomaterials, CIPS nanosheets, graphene oxide nanosheets, molybdenum disulfide nanosheets and black phosphorus nanosheets, can be applied independently or in a combination manner.

The above description is only for the purpose of illustrating the preferred examples of the present invention, and is not intended to limit the scope of the present invention. Any modifications, equivalents, improvements and the like made without departing from the spirit and principle of the present invention shall fall within the protection scope of the present invention.

What is claimed is:

1. A method of treating coronavirus-induced disease, comprising:
   administering to a subject in need thereof a composition comprising a two-dimensional nanomaterial,
   wherein the two-dimensional nanomaterial is copper indium thiophosphate nanosheet;
   wherein the two-dimensional nanomaterial inhibits binding of a spike protein of a coronavirus to a receptor ACE2 of a host cell thereof through competitively binding to a receptor binding domain (RBD) of the spike protein; and
   wherein the coronavirus is selected from one of HCoV-229E, HCoV-OC43, HCoV-NL63, HCoV-HKU1, SARS-CoV, SARS-CoV2, and MERS-CoV; and the coronavirus-induced disease is a disease caused by coronavirus infection.

2. The method according claim 1, wherein the two-dimensional nanomaterial inhibits coronavirus infection or reduces and kills the coronavirus.

3. The method according to claim 1, wherein the two-dimensional nanomaterial adsorbs the coronavirus, decomposes a protein of the coronavirus, or decomposes RNA of the coronavirus.

4. A pharmaceutical composition for treating a coronavirus-induced disease, comprising a two-dimensional nanomaterial as an active ingredient,
   wherein the two-dimensional nanomaterial is copper indium thiophosphate nanosheet;
   wherein the two-dimensional nanomaterial inhibits binding of a spike protein of a coronavirus to a receptor ACE2 of a host cell thereof through competitively binding to a receptor binding domain (RBD) of the spike protein; and
   wherein the coronavirus is selected from one of HCoV-229E, HCoV-OC43, HCoV-NL63, HCoV-HKU1, SARS-COV, SARS-COV2, and MERS-COV; and the coronavirus-induced disease is a disease caused by coronavirus infection.

5. The pharmaceutical composition according to claim 4, further comprising a therapeutically effective amount of at least one of other administered therapeutic agents or a composition thereof selected from a corticosteroid, an anti-inflammatory signal transduction modulating agent, a β2-adrenoceptor agonist, a bronchodilator, an anticholinergic medicament, a mucolytic agent, and a hypertonic saline; or a mixture thereof;
   wherein the pharmaceutical composition is in a formulation form selected from an oral formulation, an injection formulation, a mucosal administration formulation, an inhalant formulation, and an external formulation;
   wherein the pharmaceutical composition further comprises a pharmaceutically acceptable carrier or excipient.

6. A method for treating coronavirus infection, comprising administering to a subject in need thereof a therapeutically effective amount of the pharmaceutical composition according to claim 4,
   wherein the therapeutically effective amount of the two-dimensional nanomaterial is administered in a formulation form, and the formulation further comprises a pharmaceutically acceptable carrier or excipient.

7. A material for adsorbing or inhibiting a coronavirus, comprising a two-dimensional nanomaterial and a matrix, wherein the two-dimensional nanomaterial is copper indium thiophosphate nanosheet;

wherein the two-dimensional nanomaterial inhibits binding of a spike protein of a coronavirus to a receptor ACE2 of a host cell thereof through competitively binding to a receptor binding domain (RBD) of the spike protein; and wherein the coronavirus is selected from one of HCoV-229E, HCoV-OC43, HCoV-NL63, HCoV-HKU1, SARS-COV, SARS-COV2, and MERS-COV.

8. An article comprising the material according to claim 7, wherein the article is selected from a protective article, a coating material, a disinfectant, a personal care article, a packaging material, and a filtration device;

wherein the protective article is a mask, a protective suit, a protective face mask, or a protective hat;

wherein the coating material is a suspension comprising the two-dimensional nanomaterial, and the coating material can provide a coating having the two-dimensional nanomaterial on a surface of a coated object;

wherein the disinfectant is an environmental disinfectant, a wash-free hand sanitizer, a hand sanitizer and a detergent; wherein the disinfectant is used for the surface disinfection of packaging materials, medical instruments, oral instruments and cosmetic instruments;

wherein the packaging material is provided with a coating comprising the two-dimensional nanomaterial, or the packaging material is a composite material comprising the two-dimensional nanomaterial; wherein the packaging material is a packaging material used for medicaments or foods for cold chain transportation;

wherein the filtration device is a device for air filtration, a device for water body filtration and a device for mask filtration; wherein the filtration device is an air filtering net, and a surface of the air filtering net is provided with the two-dimensional nanomaterial; wherein the filtration device is an air filtering cotton, and the two-dimensional nanomaterial is attached to the air filtering cotton fiber.

9. The material according to claim 7, wherein the two-dimensional nanomaterial is a material used for preparing a protective article or for preparing a coating material, a disinfectant, a personal care article, a packaging material, or a filtering material;

wherein the protective article is a mask, a protective suit, a protective face mask, or a protective hat;

wherein the coating material is a suspension comprising the two-dimensional nanomaterial, and the coating material can provide a coating having the two-dimensional nanomaterial on a surface of a coated object;

wherein the disinfectant is an environmental disinfectant, a wash-free hand sanitizer, a hand sanitizer and a detergent; wherein the disinfectant is used for the surface disinfection of packaging materials, medical instruments, oral instruments and cosmetic instruments;

wherein the packaging material is provided with a coating comprising the two-dimensional nanomaterial, or the packaging material is a composite material comprising the two-dimensional nanomaterial; wherein the packaging material is a packaging material used for medicaments or foods for cold chain transportation;

wherein the filtering material is a material for air filtration, a material for water body filtration and a material for mask filtration; wherein the filtering material is an air filtering net, and a surface of the air filtering net is provided with the two-dimensional nanomaterial; wherein the filtering material is an air filtering cotton, and the two-dimensional nanomaterial is attached to the air filtering cotton fiber.

\* \* \* \* \*